US008063196B2

(12) United States Patent
Zheng et al.

(10) Patent No.: US 8,063,196 B2
(45) Date of Patent: Nov. 22, 2011

(54) HIGHLY ORTHOGONAL UNIVERSAL SEQUENCES FOR USE IN NUCLEIC ACID ASSAYS

(75) Inventors: Minxue Zheng, Foster City, CA (US); David Ahle, Oakland, CA (US); Brian Warner, Martinez, CA (US); Ming Wu, Redwood City, CA (US); Chu-an Chang, Piedmont, CA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 1240 days.

(21) Appl. No.: 11/049,465

(22) Filed: Feb. 1, 2005

(65) Prior Publication Data

US 2006/0172284 A1    Aug. 3, 2006

(51) Int. Cl.
*C07H 21/04* (2006.01)
*C12Q 1/68* (2006.01)
(52) U.S. Cl. .......................... 536/24.3; 435/6.1
(58) Field of Classification Search .......................... None
See application file for complete search history.

(56) References Cited

U.S. PATENT DOCUMENTS 5,681,702 A * 10/1997 Collins et al. ..................... 435/6

FOREIGN PATENT DOCUMENTS

WO    WO 96/06950    3/1996

OTHER PUBLICATIONS

Yang et al. Structural studies of a stable parallel-stranded DNA duplex incorporating isoguanine:cytosine and isocytosine:guanine basepairs by nuclear magnetic resonance spectroscopy. Biophysical Journal (1998) 75: 1163-1171.*
Kibbe, W.A. OligoCalc: an online oligonucleotide properties calculator. Nucleic Acids Research, 2007, vol. 35, Web Server issue W43-W46.*
Chen et al. Stability and Structure of RNA Duplexes Containing Isoguanosine and Isocytidine. Journal of the American Chemical Society (2001) 123(7): 1267-1274.*
Zhang et al. A Solid-Support Methodology for the Construction of Geometrical Objects from DNA. Journal of the American Chemical Society (1992) 114: 2656-2663.*
Thomas et al. Sequence Dependence of Conformations of Self-Complementary Duplex Tetradeoxynucleotides Containing Cytosine and Guanine. Biochemistry (1984) 23: 3202-3207.*
Berger, et al., "Universal bases for hybridization , replication and chain termination," Nucleic Acids Res. 28:2911-2914 (2000).
Bushnell, et al., "ProbeDesigner: for the design of probesets for branched DNA (bDNA) signal amplification assays," Bioinformatics 15:348-355 (1999).
Bustin, "Absolute quantification of mRNA using real-time reverse transcription polymerase chain reaction assays," J. Mol. Endocrinol. 25:169-193 (2000).

Collins, et al., "A branched DNA signal amplification assay for quantification of nucleic acid targets below 100 molecules/ml," Nucleic Acids Res. 25:2979-2984 (1997).
de Jager, et al., "Simultaneous detection of 15 human cytokines in a single sample of stimulated peripheral blood mononuclear cells," Clin. Diag. Lab. Immunol. 10:133-139 (2003).
Elbeik, et al., "Quantitative and cost comparison of ultrasensitive human immunodeficiency virus type 1 RNA viral load assays: Bayer bDNA quantiplex versions 3.0 and 2.0 nad Roche PCR amplicor monitor version 1.5," J. Clin. Microbiol. 38:1113-1120 (2000).
Germer, et al., "Comparative evaluation of the Versant HCV RNA 3.0, Quantiplex HCV RNA 2.0 and COBAS Amplicor HCV Monitor version 2.0 assays for quantification of hepatitic C virus in serum," J. Clin. Microbiol. 40:495-500 (2002).
Highbarger, et al., "Comparison of the quantiplex version 3.0 assay and a sensitized amplicor monitor assay for measurement of human immunodeficiency virus type 1 RNA levels in plasma samples," J. Clin. Microbiol. 37:3612-3614 (1999).
Hildesheim, et al., "Simultaneous measurement of several cytokines using small volumes of biospecimens," Cancer Epidemiol. Biomarkers Prev. 11:1477-1484 (2002).
Horn, et al., "An improved divergent synthesis of comb-type branched oligodeoxyribonucleotides (bDNA) containing multiple secondary sequences," Nucleic Acids Res. 25:4835-4841 (1997).
Horn, et al., "Chemical synthesis and characterization of branched oligodeoxyribonucleotides (bDNA) for use as signal amplifiers in nucleic acid quantification assays," Nucleic Acids Res. 25:4842-4849 (1997).
Horn and Urdea, "Forks and combs and DNA: the synthesis of branched oligodeoxyribonucleotides," Nucleic Acids Res. 17:6959-6967 (1989).
Iannone, et al., "Multiplexed single nucleotide polymorphism genotypng by oligonucleotide ligation and flow cytometry," Cytometry 39:131-140 (2000).
Kern, et al., "An enhanced-sensitivity branched-DNA assay for quantification of human immunodeficiency virus type 1 RNA in plasma," J. Clin. Microbiol. 34:3196-3202 (1996).
Lindroos, et al., "Multiplex SNP genotyping in pooled DNA samples by a four-colour microarray system," Nucleic Acids Res. 30:e70-e78 (2002).

(Continued)

*Primary Examiner* — Young J Kim
*Assistant Examiner* — Angela M Bertagna

(57) ABSTRACT

The invention provides a set of highly orthogonal six-code universal sequences for use in bDNA singleplex and multiplex nucleic acid hybridization assays. The six-code orthogonal sequences do not cross-hybridize and thus, minimize or eliminate the 3-mer cross-hybridization inherent in the second and third generation bDNA assays. The highly orthogonal universal sequences may be used in singleplex or multiplex bDNA assays quantitatively and qualitatively to determine mRNA levels in a sample; to screen for and genotype targets, such as viruses, that are present in low volumes in a sample; to screen for and genotype SNPs; and to measure changes in the amount of a gene in a sample such as when gene amplifications or deletions occur. The highly orthogonal universal sequences may also be used as universal capture probes to selectively bind assay components in a way that facilitates their further analysis.

27 Claims, 3 Drawing Sheets

OTHER PUBLICATIONS

Lindstrom and Kool, "An orthogonal oligonucleotide protecting group strategy that enables assembly of repetitive of highly structured DNA's," Nucleic Acids Res. 30:e101-e105 (2002).

Nargessi, et al., "Quantitation of estrogen receptor mRNA in breast carcinoma by branched DNA assay," Breast Cancer Res. Treat. 50:47-55 (1998).

Nurmi, et al., "A new label technology for the detection of specific polymerase chain reaction products in a closed tube," Nucleic Acids Res. 28:e28-e33 (2000).

Shen, et al., "Quantification of cytokine mRNA in peripheral blood mononuclear cells using branched DNA (bDNA) technology," J. Immunol. Met. 215:123-134 (1998).

Collins et al., A Branched DNA Signal Amplification Assay for Quantification of Nucleic Acid Targets Below 100 molecules/mL, Nucleic Acids Research 25 (15):2979-2984 (1997).

Iannone et al., Multiplexed Single Nucleotide Polymorphism Genotyping by Oligonucleotide Ligation and Flow Cytometry, Cytometry 39(2):131-140 (2000).

Shen et al., Quantification of Cytokine mRNA in Peripheral Blood Mononuclear Cells Using Branched DNA (bDNA) Technology,Journal of Immunological Methods 215 (1-2):123-134(1998).

Sigma-Genosys. Melting Temperature, 2004.

Owczarzy and Behlke, Calculation of Tm for Oligonucleotide Duplexes, Integrated DNA Technologies, 2005.

\* cited by examiner

HIGHLY ORTHOGONAL UNIVERSAL SEQUENCES FOR USE IN NUCLEIC ACID ASSAYS

FIELD OF THE INVENTION

This invention relates generally to the production of universal sequences for use in nucleic acid assays. More particularly, the invention relates to the production of highly orthogonal universal sequences that have negligible cross-reactivity when used in branched DNA ("bDNA") and other nucleic acid assays.

BACKGROUND OF THE INVENTION

The bDNA assay developed by Chiron Diagnostics and now owned by Bayer Diagnostics uses linear, rather than exponential, signal amplification to increase the sensitivity and specificity of quantitative hybridization in diagnostic tests. Collins et al., NUCLEIC ACID RESEARCH 25(15):2979-2984 (1997). The bDNA assay is used to quantify RNA and DNA targets from a variety of sources. The sensitivity and specificity of the assay are derived in part through the judicious choice of oligonucleotide probes that constitute the probe set.

In one bDNA assay, capture probes ("CPs") are attached to a solid support and capture extender ("CE") probes attach to the CPs to mediate the capture of DNA or RNA targets to the solid support. The DNA or RNA targets are labeled using a large number (typically>30) target-specific oligonucleotides called label extender ("LE") probes, which mediate the hybridization of bDNA amplifier molecules to the CEs. Hybridization of the targets to the solid support is detected typically by way of alkaline phosphatase probes, which are bound to the branches of the bDNA. The signal amplification is the product of the bound LE probes, the number of branches on the bDNA amplifier molecule, and the number of alkaline phosphatase binding sites on each branch of the bDNA molecules. This type of bDNA assay, referred to as the "first generation" bDNA assay or the "Quantiplex" bDNA assay, quantifies between 10,000 and 10,000,000 molecules/mL and has been used for the detection of HIV, HBV, and HCV. Collins et al., supra at 2979.

In the "second generation" bDNA assay, also called the "Enhanced Sensitivity" or "ES" bDNA assay, the LE probes bind preamplifiers, which in turn bind numerous bDNA amplifier molecules. The result of the second generation bDNA assays is stronger signal amplification and lower detection limits. For example, the second generation bDNA assay was able to quantify 500 molecules/mL of HIV RNA. See, Kern et al., JOURNAL OF CLINICAL MICROBIOLOGY 34(12): 3196-3202 (1996).

A negative side effect of the first and second generation bDNA assays is background noise attributed to non-specific hybridization of the amplification sequences to non-target molecules. For example, non-specific hybridization of any of the following may result in an increase in background noise: hybridization of the bDNA to the CE probe (rather than the LE probe) and non-specific hybridization of the CE probe to the LE probe (rather than the CE probe to the target and the target to the LE probe). Non-specific hybridization in the bDNA assay has the effect of reducing the sensitivity of the assay.

To reduce non-specific hybridization in the bDNA assay, the non-natural bases, isoguanosine ("iso-G") and isocytidine ("iso-C"), both of which have no detectable interaction with any of the natural DNA or RNA bases, have been incorporated into the amplification sequences. Iso-G and iso-C form standard Watson and Crick interactions with each other; however, because the hydrogen bonding pattern between the iso-G and iso-C is different from the hydrogen bonding pattern between the natural bases, there is no interaction between iso-G and iso-C and the natural bases. See, U.S. Pat. No. 5,681,702. Sequences having iso-G/iso-C base pairs are −2° C. more stable than their G/C congeners.

The incorporation of iso-G and iso-C bases into the second generation bDNA assay is known as the "third generation" bDNA assay or the "System 8" bDNA assay procedure. See, Collins et al., supra, and U.S. Pat. No. 5,681,702. In the third generation bDNA assay, preferably every third or fourth nucleotide of the capture, preamplifier, amplifier, and/or label probes are either iso-G or iso-C, both of which base pair with each other, but not with natural bases. With the incorporation of the iso-G and iso-C nucleotides into the bDNA assay, background noise resulting from non-specific hybridization is reduced and signal amplification is increased. Control over non-specific hybridization with iso-G and iso-C allows for the use of larger LE preamplifier probes, larger bDNA amplifier molecules, or more layers of amplification to improve the sensitivity of the bDNA assay, since signal can be augmented without equal amplification of noise. For example, Collins et al. document that detection of 5 attomol of oligonucleotide target with alkaline phosphatase probe has a signal to noise ("S/N") ratio of 5.5 whereas two-layered amplification has an S/N ratio of 19.6 and three-layered amplification has an S/N ratio of 154.3. Using the third generation bDNA assay, Collins et al. was able to quantify 60 molecules/mL of HIV RNA. Collins et al., supra at 1982.

The second and third generation bDNA assays have use in a multiplex format. See, Collins et al., supra at 2983. In multiplex assays, many targets are analyzed simultaneously. Multiplex assays have been used to genotype single nucleotide polymorphisms ("SNPs"), i.e., single point variations in genomic DNA, and to screen for various cytokines in a sample. See, Iannone et al., CYTOMETRY 39:131-140 (2000); Collins et al., supra at 2983; and de Jager et al., CLINICAL AND DIAGNOSTIC LABORATORY IMMUNOLOGY 10(1):133-139 (2003).

SNPs represent the most abundant form of a genetic variation and occur, on average, at every 1-2 kb in the human genome. Over 4 million SNPs have been identified (see, www.ncbi.nlm.nih.gov/SNP), and of these SNPs over 1.2 million have been mapped to the human genome (see, snp.cshl.org). Due to the abundant repetitive sequences in the human genome, all of the SNPs contained in the databases are not necessarily true polymorphisms or they may not be polymorphic in a specific population of interest. The identification of SNPs has uses beyond human diagnostic analyses. For example, the identification of SNPs is useful for genetic mapping, genetic diversity analyses, and marker-assisted breeding in a wide-variety of species including, plants, mammals, and micro-organisms. Accordingly, accurate and efficient genotyping is a prerequisite to the identification of SNPs. See, Lindroos et al., NUCLEIC ACID RESEARCH 30(14):1-9 (2002).

Cytokines are soluble proteins that are secreted by cells of the immune system. These proteins can alter the behavior and properties of different cell types. Different cytokines possess biological overlapping functions and therefore, have the ability to regulate the production of other cytokines. Thus, analysis of the function of a complete set of cytokines within a microenvironment, i.e., a site of inflammation, is frequently of more value than analysis of a single isolated cytokine. Cytokines can be quantitated at various levels. Multiplex assays for detection of cytokines at the messenger RNA ("mRNA") and cellular levels have limitations, such as the need for large volumes of sample or detection of a precursor protein rather than a native protein. See, de Jager et al., supra.

In order to use the bDNA assay in a multiplex format, multiple CP and CE sequences must be used in order to attach multiple targets to the solid support. Collins et al., supra. The problem with using the six-base code second and third generation bDNA assays in multiplex format is the potential 3-mer cross-hybridization that may occur between the natural bases of the multiple targets and the capture, preamplifier, amplifier, and label probes. More specifically, as mentioned above, the second and third generation bDNA assays both have a non-natural base in every fourth nucleotide position of the capture, preamplifier, amplifier, and/or label probes; accordingly, under this design, three of four potential natural bases are positioned between two non-natural bases in each of the probes. Since each natural base has only one successful match, hybridization of a natural base with any one of its three mismatched bases will result in a significant decrease in the efficacy of the multiplex bDNA assay. Further, as complicated multiplex assays are developed, unwanted cross-reactivity between analytes will be difficult to trouble-shoot and remove.

Accordingly, there remains a need in the art to design and generate multiple highly specific sequences for use in bDNA singleplex and multiplex assays that do not cross-hybridize. The present invention addresses this need in the art by designing and generating highly orthogonal six-code universal sequences that minimize or eliminate the 3-mer cross-hybridization inherent in the second and third generation bDNA assays as they are presently known in the art. By developing universal sequences with little or no cross-reactivity, the accuracy of bDNA assays for the detection and screening of viruses, retroviruses, SNPs, cytokines, and gene amplifications and deletions, is dramatically improved.

SUMMARY OF THE INVENTION

To address the need in the art for multiple highly specific sequences for use in bDNA singleplex and multiplex assays that do not cross-hybridize, the present invention provides in one aspect of the invention, a highly orthogonal six-base universal sequence comprised of four natural bases and two non-natural bases, wherein one to four of the natural bases, arranged in no specific order, are selected from the group consisting of guanosine (G), cytosine (C), adenosine (A), and thymidine (T) or uracil (U) and are separated by one or both of the non-natural bases such that approximately 50% of the sequence is comprised of G/C bases and the sequence has a melting temperature (Tm) of approximately 80-85° C.

In another aspect of the invention, there is provided a method for preparing highly orthogonal universal sequences for hybridization comprising the steps of (a) preparing 5' to 3' sequences from six nucleotide bases comprised of four natural bases selected from the group consisting of guanosine (G), cytosine (C), adenosine (A), and thymidine (T) or uracil (U) and two non-natural bases, wherein the sequences are comprised of one to four of the natural bases arranged in no specific order and separated by one or both of the two non-natural bases; (b) screening the sequences and selecting only those sequences having a G/C concentration of 50% or more; (c) testing the melting temperature (Tm) of the sequences and selecting only those sequences with a Tm of approximately 80-85° C.; (d) cross-hybridizing the sequences individually with identical sequences and with complementary sequences; and (e) selecting only those sequences with at most 3-mer interactions with the identical sequences.

In both aspects of the invention, it is preferred that the non-natural base is selected from the group consisting of isoguanosine and isocytosine and the sequences range in length from 20 to 25 bases with a Tm of approximately 85° C.

The highly orthogonal universal sequences of the present invention may be used in singleplex or multiplex bDNA assays to quantify mRNA in a sample; to detect and genotype viruses, retroviruses, and SNPs in a sample; and to measure gene amplifications or deletions in a sample. The highly orthogonal universal sequences may also be used as universal capture probes in nucleic acid assays in general where it is useful to selectively bind assay components to a substrate in a way that facilitates their further analysis.

Additional aspects, advantages and features of the invention will be set forth, in part, in the description that follows, and, in part, will become apparent to those skilled in the art upon examination of the following, or may be learned by practice of the invention.

BRIEF DESCRIPTION OF THE DRAWINGS

The file of this patent contains at least one drawing executed in color. Copies of this patent or patent application publication with the color drawing will be provided by the Patent and Trademark Office upon request and payment of the necessary fee.

DETAILED DESCRIPTION OF THE INVENTION

Definitions and Nomenclature

Figure 1A:
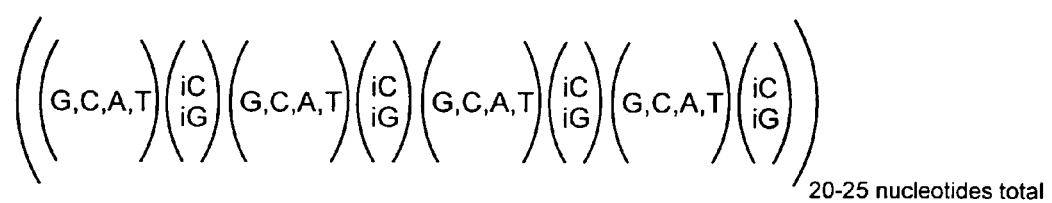
FIG. 1A depicts a formula that serves as a starting point for the preparation of the orthogonal universal sequences of the present invention.

Before describing detailed embodiments of the invention, it will be useful to set forth definitions that are used in describing the invention. The definitions set forth apply only to the terms as they are used in this patent and may not be applicable to the same terms as used elsewhere, for example in scientific literature or other patents or applications including other applications by these inventors or assigned to common owners. The following description of the preferred embodiments and examples are provided by way of explanation and illustration. As such, they are not to be viewed as limiting the scope of the invention as defined by the claims. Additionally, when examples are given, they are intended to be exemplary only and not to be restrictive. For example, when an example is said to "include" a specific feature, that is intended to imply that it may have that feature but not that such examples are limited to those that include that feature.

It must be noted that, as used in this specification and the appended claims, the singular forms "a," "an," and "the" include plural referents unless the context clearly dictates otherwise. Also, the use of the terms "optional" or "optionally" means that the subsequently described event or circumstance may or may not occur, and that the description includes instances where the said event or circumstance occurs as well as instances where it does not.

In describing and claiming the present invention, the following terminology will be used in accordance with the definitions set out below.

The term "orthogonal sequence" refers to sequences that are in perfectly matched Watson-Crick interactions. For example, the sequence ATCG is orthogonal to the sequence TAGC within a double helix. Nucleic acids having highly orthogonal sequences are typically free of undesirable secondary structures.

The term "universal sequences" or "universal probes," which are used interchangeably herein, refers to sequences or probes that may be used to test many different samples, in other words, universal sequences or universal probes are independent of the sequences being analyzed. Thus, the "highly orthogonal universal sequences" of the present invention refers to sequences that have strict Watson-Crick interactions that are not tailored to identify a specific sample, but rather, may be used to screen for a variety of samples, such as, for example, in a multiplex assay. As noted herein, the highly orthogonal universal probes of the present invention are isothermal, with uniform kinetics, and exhibit minimal non-specific cross hybridization.

The term "nucleic acid analyte" refers to a nucleic acid, i.e., DNA or RNA, that subject to analysis.

The term "target" refers to molecule, gene, or genome, containing a nucleic acid sequence or sequence segment that is intended to be characterized by way of identification, quantification, or amplification. Targets contemplated under the invention may be derived from any organism, including mammalian and non-mammalian animals, bacteria, viruses, or fungi. A retrovirus is one example of a target that can be identified or quantified using the highly orthogonal universal sequences of the present invention in a bDNA assay. It is to be understood that where appropriate, the terms "nucleic acid analyte," "target," and "target nucleic acid analyte" may be used interchangeably to identify a nucleic acid, nucleic acid sequence, or nucleic acid sequence segment within an organism, bacteria, or virus, that is subject to characterization.

As used herein, the term "sample" refers to a fluid or tissue obtained from an organism, such as a human, that contains a nucleic acid analyte to be characterized. Such samples are known in the art and include, without limitation, blood, plasma, serum, spinal fluid, lymph fluid, cell lysates, tears, saliva, semen, milk, and secretions of the skin, respiratory, intestinal, or gastrointestinal tract. The nucleic acid analyte of interest may be genetic material from the host or non-host genetic material. Thus, for example, samples obtained from a human individual may contain human genetic material and/or the genetic material of an infectious pathogen such as a bacterium, virus, or fungus. These samples described herein may be obtained from biological tissue or fluid samples using conventional techniques such as, for example, needle biopsy or swabbing.

As used herein, the term "virus" is used to refer generally to both DNA viruses and RNA viruses, the latter known as "retroviruses." It is understood by those of ordinary skill in the art that DNA viruses replicate by integrating DNA into the host genome and retroviruses replicate by integrating RNA into the host genome. When screening for DNA viruses, the double stranded viral DNA must be released from the viral protein coating and denatured in order to separate the two strands. The single-stranded viral DNA is then hybridized to the capture probes, which are bound to a substrate and the bDNA molecules are used to amplify the single stranded DNA. When screening for RNA retroviruses, the viral RNA is released from the viral protein coating and hybridized to the bound capture probes. Because viral RNA is not double stranded, a denaturation step is not necessary. Within the context of the present invention, it is understood that the bDNA assays may be used to screen for both DNA viruses and retroviruses.

The term "gene" refers to a particular nucleic acid sequence within a DNA molecule that occupies a precise locus on a chromosome and is capable of self-replication by coding for a specific polypeptide chain. The term "genome" refers to a complete set of genes in the chromosomes of each cell of a specific organism.

The term "gene amplification" refers to an increase in the number of copies of a specific gene in an organism's genome. It is understood by one of ordinary skill in the art that the presence of multiple copies of a gene within a genome may result in the production of a corresponding protein at elevated levels.

It will be appreciated that, as used herein, the terms "nucleotide" and "nucleoside" refer to nucleosides and nucleotides containing not only the four natural DNA nucleotidic bases, i.e., the purine bases guanine (G) and adenine (A) and the pyrimidine bases cytosine (C) and thymine (T), but also the RNA purine base uracil (U), the non-natural nucleotide bases iso-G and iso-C, universal bases, degenerate bases, and other modified nucleotides and nucleosides. Universal bases are bases that exhibit the ability to replace any of the four normal bases without significantly affecting either melting behavior of the duplexes or the functional biochemical utility of the oligonucleotide. Examples of universal bases include 3-nitropyrrole and 4-, 5-, and 6-nitroindole, and 2-deoxyinosine (dI), that latter considered the only "natural" universal base. While dI can theoretically bind to all of the natural bases, it codes primarily as G. Degenerate bases consist of the pyrimidine derivative 6H,8H-3,4-dihydropyrimido[4,5-c][1,2]oxazin-7-one (P), which when introduced into oligonucleotides base pairs with either G or A, and the purine derivative N6-methoxy-2,6-diaminopurine (K), which when introduced into oligonucleotides base pairs with either C or T. Examples of the P and K base pairs include P-imino, P-amino, K-imino, and K-amino.

Modifications to nucleotides and nucleosides include, but are not limited to, methylation or acylation of purine or pyrimidine moieties, substitution of a different heterocyclic ring structure for a pyrimidine ring or for one or both rings in the purine ring system, and protection of one or more functionalities, e.g., using a protecting group such as acetyl, difluoroacetyl, trifluoroacetyl, isobutyryl, benzoyl, and the like. Modified nucleosides and nucleotides also include modifications on the sugar moiety, e.g., wherein one or more of the hydroxyl groups are replaced with halide and/or hydrocarbyl substituents (typically aliphatic groups, in the latter case), or are functionalized as ethers, amines, or the like. Examples of modified nucleotides and nucleosides include, but are not limited to, 1-methyladenine, 2-methyladenine, $N^6$-methyladenine, $N^6$-isopentyl-adenine, 2-methylthio-$N^6$-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromo-guanine, 8-chloroguanine, 8-aminoguanine, 8-methylguanine, 8-thioguanine, 5-fluoro-uracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)

uracil, 5-(methyl-aminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine, and 2,6-diaminopurine.

As used herein, the term "oligonucleotide" encompasses polydeoxyribonucleotides (containing 2-deoxy-D-ribose), polyribonucleotides (containing D-ribose), any other type of polynucleotide that is an N-glycoside of a purine or pyrimidine base, and other polymers containing normucleotidic backbones (e.g., protein nucleic acids and synthetic sequence-specific nucleic acid polymers commercially available from the Anti-Gene Development Group, Corvallis, Oreg., as Neugene™ polymers) or nonstandard linkages, providing that the polymers contain nucleobases in a configuration that allows for base pairing and base stacking, such as is found in DNA and RNA. Thus, "oligonucleotides" herein include double- and single-stranded DNA, as well as double- and single-stranded RNA and DNA:RNA hybrids, and also include known types of modified oligonucleotides, such as, for example, oligonucleotides wherein one or more of the naturally occurring nucleotides is substituted with an analog; oligonucleotides containing internucleotide modifications such as, for example, those with uncharged linkages (e.g., methyl phosphonates, phosphotriesters, phosphoramidates, carbamates, etc.), negatively charged linkages (e.g., phosphorothioates, phosphorodithioates, etc.), and positively charged linkages (e.g., aminoalkylphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), and those containing alkylators. There is no intended distinction in length between the terms "polynucleotide" and "oligonucleotide," and these terms will be used interchangeably. These terms refer only to the primary structure of the molecule. As used herein the symbols for nucleotides and polynucleotides are according to the IUPAC-IUBMB Joint Commission on Biochemical Nomenclature (see, www.chem.qmul.ac.uk/iupac/jcbn).

Oligonucleotides can be synthesized by known methods. Background references that relate generally to methods for synthesizing oligonucleotides include those related to 5'-to-3' syntheses based on the use of β-cyanoethyl phosphate protecting groups. See, e.g., de Napoli et al., Gazz Chim Ital 114:65 (1984); Rosenthal et al., Tetrahedron Lett 24:1691 (1983); Belagaje and Brush, Nuc Acids Res 10:6295 (1977); in references which describe solution-phase 5'-to-3' syntheses include Hayatsu and Khorana, J Am Chem Soc 89:3880 (1957); Gait and Sheppard, Nuc Acids Res 4: 1135 (1977); Cramer and Koster, Angew Chem Int Ed Engl 7:473 (1968); and Blackburn et al., J Chem Soc Part C, at 2438 (1967). Additionally, Matteucci and Caruthers, J Am Chem Soc 103: 3185-91 (1981) describes the use of phosphochloridites in the preparation of oligonucleotides; Beaucage and Caruthers, Tetrahedron Lett 22:1859-62 (1981), and U.S. Pat. No. 4,415,732 to Caruthers et al. describe the use of phosphoramidites for the preparation of oligonucleotides. Smith, Am Biotech Lab, pp. 15-24 (December 1983) describes automated solid-phase oligodeoxyribonucleotide synthesis; and T. Horn and M. S. Urdea, DNA 5:421-25 (1986) describe phosphorylation of solid-supported DNA fragments using bis(cyanoethoxy)-N,N-diisopropylaminophosphine. See also, references cited in Smith, supra; Warner et al., DNA 3:401-11 (1984); and T. Horn and M. S. Urdea, Tetrahedron Lett 27:4705-08 (1986).

The terms "complementary" and "substantially complementary" refer to base pairing between nucleotides or nucleic acids, such as, for instance, between the two strands of a double-stranded DNA molecule or between an oligonucleotide primer and a primer binding site on a single-stranded nucleic acid to be sequenced or amplified. Complementary nucleotides are, generally, A and T (or A and U), and G and C.

As used herein, the term "probe" refers to a structure comprised of a polynucleotide that forms a hybrid structure with a target sequence contained in a molecule (i.e., a "target molecule") in a sample undergoing analysis, due to complementarity of at least one sequence in the probe with the target sequence. The nucleotides of any particular probe may be deoxyribonucleotides, ribonucleotides, and/or synthetic nucleotide analogs.

The term "primer" refers to a molecule that comprises an oligonucleotide, whether produced naturally as in a purified restriction digest or produced synthetically, which is capable of acting as a point of initiation of synthesis when placed under conditions in which synthesis of a primer extension product that is complementary to a nucleic acid strand is induced, i.e., in the presence of appropriate nucleotides and an agent for polymerization such as a DNA polymerase in an appropriate buffer and at a suitable temperature.

The term "hybridizing conditions" is intended to mean those conditions of time, temperature, and pH, and the necessary amounts and concentrations of reactants and reagents, sufficient to allow at least a portion of complementary sequences to anneal with each other. As is well known in the art, the time, temperature, and pH conditions required to accomplish hybridization depend on the size of the oligonucleotide probe to be hybridized, the degree of complementarity between the oligonucleotide probe and the target, and the presence of other materials in the hybridization reaction admixture. The actual conditions necessary for each hybridization step are well known in the art or can be determined without undue experimentation. Typical hybridizing conditions include the use of solutions buffered to a pH from about 7 to about 8.5 and temperatures of from about 30° C. to about 60° C., preferably from about 37° C. to about 55° C. for a time period of from about one second to about one day, preferably from about 15 minutes to about 16 hours, and most preferably from about 15 minutes to about three hours.

"Hybridization conditions" also include an effective buffer. Any buffer that is compatible, i.e., chemically inert, with respect to the probes and other components, yet still allows for hybridization between complementary base pairs, can be used. One particularly preferred buffer comprises 3xSSC, 50% formamide, 10% dextran sulfate (MW 500,000), 0.2% casein, 10 µg/mL poly A, and 100 µg/mL denatured salmon sperm DNA, wherein 1xSSC is 0.15 M sodium chloride and 0.015 M sodium citrate. Another particularly preferred buffer comprises 5xSSC, 0.1 to 0.3% sodium dodecyl sulfate, 10% dextran sulfate, 1 mM $ZnCl_2$, and 10 mM $MgCl_2$, wherein 1xSSC is as defined above. Other suitable buffers are known to those of ordinary skill in the art.

It is understood by one of ordinary skill in the art that the isolation of DNA and RNA target sequences from a sample requires different hybridization conditions. For example, if the sample is initially disrupted in an alkaline buffer, double stranded DNA is denatured and RNA is destroyed. By contrast, if the sample is harvested in a neutral buffer with SDS and proteinase K, DNA remains double stranded and cannot hybridize with the probes and the RNA is protected from degradation.

The term "substrate" refers to any solid or semi-solid surface to which a desired oligonucleotide may be anchored. Suitable substrates include any material that can immobilize an oligonucleotide and encompass, for example, glass, nitrocellulose, plastics including polyvinyl chloride (e.g., in sheets or microtiter wells), polystyrene latex (e.g., in beads or microtiter plates), polyvinylidine fluoride (e.g., in microtiter plates), polystyrene (e.g., in beads), metal, polymer gels, and the like.

The term "support" refers to any solid surface (including semi-solid surfaces) to which a probe, analyte molecule, or other chemical entity may be anchored. Suitable support materials include, but are not limited to, supports that are typically used for solid phase chemical synthesis, e.g., polymeric materials (e.g., polystyrene, polyvinyl acetate, polyvinyl chloride, polyvinyl pyrrolidone, polyacrylonitrile, polyacrylamide, polymethyl methacrylate, polytetrafluoroethylene, polyethylene, polypropylene, polyvinylidene fluoride, polycarbonate, divinylbenzene styrene-based polymers), agarose (e.g., Sepharose®), dextran (e.g., Sephadex®), cellulosic polymers and other polysaccharides, silica and silica-based materials, glass (particularly controlled pore glass) and functionalized glasses and ceramics. Preferred supports are solid substrates in the form of beads or particles, including microparticles and nanoparticles.

The term "label" as used herein refers to any atom or molecule that can be used to provide a detectable (preferably quantifiable) signal, and that can be attached to a nucleic acid or protein via a covalent bond or noncovalent interaction (e.g., through ionic or hydrogen bonding, or via immobilization, adsorption, or the like). Labels generally provide signals detectable by fluorescence, chemiluminescence, radioactivity, colorimetry, mass spectrometry, X-ray diffraction or absorption, magnetism, enzymatic activity, or the like. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase (HRP) is usually detected by its ability to convert 3,3',5,5'-tetramethylbenzidine (TMB) to a blue pigment, quantifiable with a spectrophotometer. It should be understood that the above description is not meant to categorize the various labels into distinct classes, as a single label may be detected using two or more different methods. For example, $^{125}I$ can serve as a radioactive label and as an electron-dense reagent. HRP may serve as an enzyme or as an antigen for a monoclonal antibody (mAb). Further, one may combine various labels for a desired effect. For example, mAbs and avidin also require labels in the practice of this invention; thus, one might label a probe with biotin, and detect its presence with avidin labeled with 125I, or with an anti-biotin mAb labeled with HRP, or with an HRP molecule conjugated to avidin or streptavidin. Other permutations and possibilities will be readily apparent to those of ordinary skill in the art, and are considered as equivalents.

The term "target amplification" refers to a procedure that amplifies a gene or portion of a gene, such as, for example, PCR or linear amplification (see, Phillips and Eberwine, METHODS 10(3):283-288 (1996)).

The term "PCR" refers to the polymerase chain reaction ("PCR") technique, disclosed in U.S. Pat. No. 4,683,195 to Mullis et al. and U.S. Pat. No. 4,683,202 to Mullis, both incorporated herein by reference. Briefly, in the PCR technique, a sample of DNA is mixed in a solution with a molar excess of two oligonucleotide primers of 10-30 base pairs each that are prepared to be complementary to the 3' end of each strand of the DNA duplex; a molar excess of unattached nucleotide bases (dNTPs); and DNA polymerase, (preferably Taq polymerase, which is stable to heat), which catalyzes the formation of DNA from the oligonucleotide primers and dNTPs. Of the two primers, one is a forward primer that will bind in the 5'-3' direction to the 3' end of one strand of the denatured DNA analyte and the other is a reverse primer that will bind in the 3'-5' direction to the 3' end of the other strand of the denatured DNA analyte. The solution is heated to 94-96° C. to denature the double-stranded DNA to single-stranded DNA. When the solution cools, the primers bind to the separated strands and the DNA polymerase catalyzes a new strand of analyte by joining the dNTPs to the primers. When the process is repeated and the extension products synthesized from the primers are separated from their complements, each extension product serves as a template for a complementary extension product synthesized from the other primer. In other words, an extension product synthesized from the forward primer, upon separation, would serve as a template for a complementary extension product synthesized from the reverse primer. Similarly, the extension product synthesized from the reverse primer, upon separation, would serve as a template for a complementary extension product synthesized from the forward primer. In this way, the region of DNA between the primers is selectively replicated with each repetition of the process. Since the sequence being amplified doubles after each cycle, a theoretical amplification of one billion copies may be attained after repeating the process for a few hours; accordingly, extremely small quantities of DNA may be amplified using PCR in a relatively short period of time.

Where the starting material for the PCR reaction is RNA, complementary DNA ("cDNA") is made from RNA via reverse transcription. The resultant cDNA is then amplified using the PCR protocol described above. Reverse transcriptases are known to those of ordinary skill in the art as enzymes found in retroviruses that can synthesize complementary single strands of DNA from an mRNA sequence as a template. The enzymes are used in genetic engineering to produce specific cDNA molecules from purified preparations of mRNA. A PCR used to amplify RNA products is referred to as reverse transcriptase PCR or "RT-PCR."

The term "singleplex" refers to a single assay that is not carried out simultaneously with any other assays. Singleplex assays do include individual assays that are carried out sequentially. Generally the assays are hybridization assays.

The term "multiplex" refers to multiple assays that are carried out simultaneously, in which detection and analysis steps are generally performed in parallel. As used herein, a multiplex assay may also be termed according to the number of target molecules that the assay aims to identify. For example, a multiplex assay that is designed to identify six cytokines may be referenced a "sixplex" assay and a multiplex assay that is designed to identify eleven cytokines may be referenced an "elevenplex" assay. Like singleplex assays, multiplex assays are typically hybridization assays.

As used herein, the term "a bDNA assay" refers to both singleplex and multiplex bDNA assays, unless specified otherwise.

Although any similar or equivalent methods and materials may be employed in the practice or testing of the present invention, preferred methods and materials are now described.

The Orthogonal Sequences:

In a one embodiment of the invention, there is provided a highly orthogonal six-base universal sequence comprised of four natural bases and two non-natural bases, wherein one to four of the natural bases, arranged in no specific order, are selected from the group consisting of guanosine (G), cytosine (C), adenosine (A), and thymidine (T) or uracil (U) and are separated by one or both of the non-natural bases such that approximately 50% of the sequence is comprised of G/C bases and the sequence has a melting temperature (Tm) of approximately 80-85° C.

In a preferred embodiment of the invention, the two non-natural bases are isoguanine or isocytosine. As shown in Example 2, it is also preferred that the sequences have a Tm of approximately 85° C. Ideally, the sequences range in length from 20 to 25 bases, although as is understood by one of ordinary skill in the art, the length of the sequences will vary depending on their intended use. For example, under some circumstances it may be preferable for the sequences to be less than a 20-mer or longer than a 25-mer. In this respect, sequences ranging from 10-50 bases in length are contemplated under the present invention, with sequences ranging from 15-30 bases, preferred, and sequences ranging from 20-25 bases most preferred.

As noted above, the four natural bases of the claimed orthogonal universal sequence are selected from the group consisting of the following nucleotides: guanosine (G), cytosine (C), adenosine (A), and thymidine (T) where DNA is hybridized; and guanosine (G), cytosine (C), adenosine (A), and uracil (U) where RNA is hybridized. Guanosine and adenosine are purines, which consist of a fused six-membered and five-membered nitrogen-containing ring, while cytosine, thymidine, and uracil, are purines, which consist of a six-membered nitrogen containing ring. The natural base nucleotides form the purine-pyrimidine base pairs G/C and A/T (U). The binding energy of the G/C base pair is greater than that of the A/T base pair due to the presence of three hydrogen-bonding moieties in the former compared with two in the latter, as shown below:

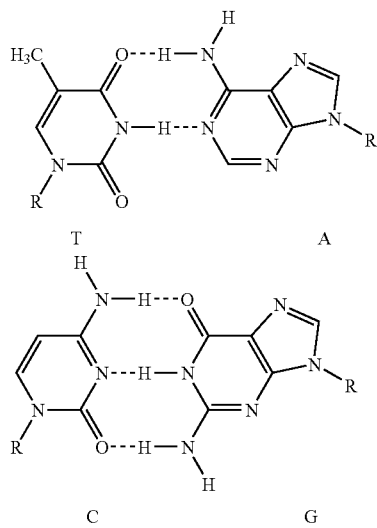

Due to the higher binding energy of the G/C base pair, the melting temperature (Tm) (i.e., the temperature at which 50% of the sequence is annealed to its complement) of G/C rich sequences is higher than sequences with A/T rich content.

The Tm of a sequence may be increased though any of the following methods: increasing the G/C content of the sequence; increasing the length of the molecule, i.e., longer DNA has a higher Tm than shorter DNA; increasing the ionic strength of the sequences (to increase positive ions and decrease the repelling forces in the DNA backbone); adjusting the pH of the sequences (because extreme pH values can ionize bases and disrupt the H bonds, Tm decreases drastically outside pH 5-9); and careful selection of solvents (organic solvents being known to lower Tm). A formula for determining the Tm applicable in water solutions around neutral pH is the "% G/C-method":

$$Tm(° C.)=81.5° C.+16.6(\log [Na^+])+0.41(\% GC)-675/n,$$

where n is the number of nucleotides in the sequence. By calculating the Tm with this formula, the annealing temperature of a sequence may be determined without resorting to physically measuring the sequence with UV spectrometry. Using such a formula is useful when the annealing temperature of a sequence must be predicted for setting a PCR protocol.

Another formula widely used to determine the annealing temperature of a sequence is the following shorter formula.

$$Td(° C.)=2[A+T]+4[C+G].$$

This formula, which determines the disassociation temperature (Td) (i.e., the temperature at which 50% of the sequence is annealed to its membrane-bound complement), rather than the Tm, has been found to be accurate for sequences in the 14-20 base pair range. When this formula is used, the annealing temperature of the sequence for PCR purposes is generally calculated as Td-5. Thus, for example, if the oligonucleotides CP1 or CE1 at Table 1 are used as PCR primers, the annealing temperature of the primers would be 69.7° C. (the Td) minus 5 or 64.7° C.

Other formulas for predicting the Tm of nucleotide sequences are known to those of ordinary skill in the art and include, for example, the "nearest neighbor" method, which is explained at the following website: micro.nwfsc.noaa.gov/protocols/methods/DNA-PCRMethodsDocs/10-2002/10.8.02.2167.html. A discussion of alternative formulas for predicting Tm of nucleotide sequences is set forth in Ahsen et al., CLINICAL CHEMISTRY 47(11):1956-1961 (2001).

Within the context of the present invention, it is preferred that the highly orthogonal sequences have a Tm of approximately 80° C., with a Tm of 85° C. more preferred. It is to be understood that the 80-85° C. Tm range is the preferred range for the highly orthogonal universal sequences and that under some circumstances, Tms below 80° C. or above 85° C. may be preferred. Thus, under some circumstances, a Tm of approximately 75° C. or 90° C. may be the preferred Tm for the sequences. As noted above, the G/C content in the orthogonal universal sequences may affect the Tm of the sequences. Thus, while it is most preferred that the G/C content of the orthogonal universal sequences is approximately 50%, it is to be understood that sequences with G/C concentrations greater than 50% are contemplated under the present invention; thus, under certain circumstances it may be preferred to have a sequence with a G/C concentration that is greater than 50%, such as for example, sequences with G/C concentrations in the range of 51% through 75% or greater.

The two non-natural bases of the orthogonal universal sequences of the present invention are preferably iso-G and iso-C. As noted previously, the hydrogen bonding pattern between iso-G and iso-C is different from the hydrogen bonding pattern between G and C and thus, iso-G and iso-C do not interact with natural bases; the bonding pattern of iso-G and iso-C is shown below:

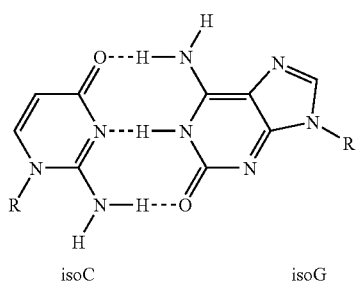

isoC    isoG

While preferred sequences of the present invention range in length from 20 to 25 bases, it is to be understood that under some circumstances it may be preferable for the sequences to be less than a 20-mer or longer than a 25-mer.

The highly orthogonal universal sequences of the present invention may be prepared by the following method: (a) preparing 5' to 3' sequences from six nucleotide bases comprised of four natural bases selected from the group consisting of guanosine (G), cytosine (C), adenosine (A), and thymidine (T) or uracil (U) and two non-natural bases, wherein the sequences are comprised of one to four of the natural bases arranged in no specific order and separated by one or both of the two non-natural bases; (b) screening the sequences and selecting only those sequences having a G/C concentration of 50% or more; (c) testing the melting temperature (Tm) of the sequences and selecting only those sequences with a Tm of approximately 80-85° C.; (d) cross-hybridizing the sequences individually with identical sequences and with complementary sequences; and (e) selecting only those sequences with at most 3-mer interactions with the identical sequences.

Figure 1B:
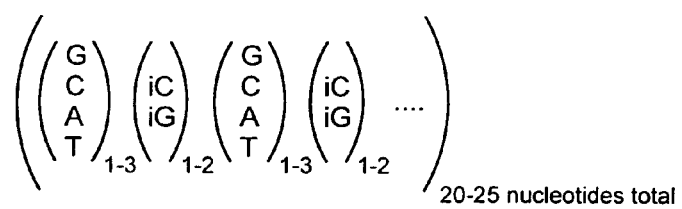
FIG. 1B depicts the formula for the orthogonal universal sequences of the present invention; the depicted sequences range in length from 20 to 25 bases, have a G/C concentration of approximately 50%, melting points between 80-85° C., and minimal cross-reactivity.

FIG. 1A shows a generic structure of the claimed orthogonal sequences. FIG. 1B shows the orthogonal sequences rearranged to have approximately 50% G/C composition and a melting point of approximately 80-85° C. Example 2 describes the production of the probes depicted in FIG. 1B, and which were derived, as described in Example 2, from the generic structure of FIG. 1A. As previously noted, it is preferred that the non-natural base is selected from the group consisting of isoguanosine and isocytosine and that the sequences range in length from approximately 20 to 25 bases with a Tm of approximately 85° C.

Signal Detection:

As previously noted, the highly orthogonal universal sequences of the present invention are used as the CPs, CEs, LEs, or amplifier probes of the bDNA assay (see, Examples 2-4) with signal amplification of the bDNA assay resulting from the bound LE probes, the number of branches on the bDNA amplifier molecules, and the number of alkaline phosphatase, or other enzyme labeled binding sites, on each branch of the bDNA amplifier probes.

Any type of label can be used to detect the signal amplification products described herein and labeling of the bDNA amplifier probes can be accomplished by any means known in the art; such procedures are generally dependent upon the nature of the label. Preferred labels include those moieties detectable by spectroscopic, photochemical, biochemical, immunochemical, or chemical means. Such labels include, without limitation, fluorescers, chemiluminescers, dyes, biotin, haptens, enzymes, enzyme substrates, enzyme cofactors, enzyme inhibitors, enzyme subunits, metal ions, electron-dense reagents, and radioactive isotopes (e.g., $^{32}P$). The label moiety can be directly or indirectly attached to the amplicon. Preferably, the label should be selected to withstand denaturing conditions if it is to be attached directly to the primer. It is preferred, although not necessary, that the label be biotin, which can be detected via binding with streptavidin coupled to a fluorescer, e.g., a streptavidin-phycoerythrin conjugate.

For fluorescers, a large number of fluorometers are available. For chemiluminescers, luminometers or films are available. With enzymes, a fluorescent, chemiluminescent, or colored product can be provided and determined fluorometrically, luminometrically, spectrophotometrically, or visually (preferably with the aid of a microscope). For example, a biotinylated label is detected by adding a streptavidin-phycoerythrin conjugate, followed by detection of phycoerythrin-induced fluorescence.

Each signal provided by the solid substrate is detected by any conventional means. For example, the signal can be based on the shape of the substrate, wherein the first detectable signal and second detectable signal are differentiated by different shapes of the corresponding solid substrate. It is preferred, however, that each set of solid substrates, e.g., the plurality of first solid substrates, generates a signal unique to the plurality. Thus, for example, each of the first solid substrates has a first detectable signal and each of the second solid substrates has a second detectable signal. Again, the first and second detectable signals can be provided by moieties selected from the groups consisting of fluorescers, chemiluminescers, dyes, biotin, haptens, enzymes, enzyme substrates, enzyme cofactors, enzyme inhibitors, enzyme subunits, metal ions, electron-dense reagents, and radioactive isotopes.

It is most preferred, however, that the solid substrates be beads, wherein a detectable signal is provided by one or more fluorescent dyes. Examples of suitably dyed substrates, e.g., beads, are described in U.S. Pat. No. 6,268,222 to Chandler et al. As described therein, the solid substrates comprise a combination of fluorescent or colored dyes. Preferred dyes include cyanine dyes that are characterized by having emission wavelengths of between 550 nm to 900 nm. Some cyanine dyes have a blue to blue-green fluorescence, while others have green to yellow-green fluorescence. Still other cyanine dyes have red or even infrared fluorescence. The cyanine dye, or any other conventional dye, can be covalently attached to the substrate or adsorbed, e.g., "stained," thereon. In addition, the substrate can have attached thereto one or more populations of fluorescently stained nanoparticles, wherein all nanoparticles in a given population have the same dye concentration. By varying the quantity and ratio of different dyes specific to different populations of nanoparticles associated with the substrate, it is possible to establish and distinguish a large number of discreet populations of substrates with unique emission spectra. Such uniquely labeled substrates are particularly useful for multiplex analysis of sequences, and can be conveniently detected and analyzed using flow cytometry. Such beads are also available from commercial suppliers such as, for example, Luminex Corporation (Austin, Tex.).

Substrates having a diameter of less than one millimeter can be used in flow cytometers, although other sized particles can be used as well. It is preferred, however, that substrates that are spherical in shape, e.g., beads, be used. Such beads have a size in the range of from about 0.1 to 1,000 μm, preferably 1 to 100 μm, more preferably 2 to 50 μm, still more preferably 3 to 25 μm, with beads having a diameter of from about 3 to 10 μm being most preferred. Beads of this size are suited for use in flow cytometers, thereby providing a facile means for detecting and counting the complexes.

The solid substrates are preferably, although not necessarily, made of a polymeric material such as polystyrene. Other usable polymeric materials include brominated polystyrene, polyacrylic acid, polyacrylonitrile, polyamide, polyacrylamide, polyacrolein, polybutadiene, polycaprolactone, polycarbonate, polyester, polyethylene, polyethylene terephthalate, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, polylactide, polyglycolide, poly(lactide-co-glycolide), polyanhydride, polyorthoester, polyphosphazene, polyphosophaze, polysulfone, and combinations thereof. These polymers may also incorporate a magnetic or magnetically responsive metal oxide selected from the group consisting of superparamagnetic, paramagnetic, ferrimagnetic, antiferromagnetic, and ferromagnetic metal oxides.

Utility:

The highly orthogonal universal sequences of the claimed invention have utility in a variety of applications, such as, for example, diagnostic assays and genetic analyses. Specifically, the highly orthogonal universal sequences may be used in singleplex or multiplex bDNA assays quantitatively and qualitatively to determine mRNA levels in a sample; to screen for gene amplification products in a sample; to screen for and genotype targets, such as viruses, that are present in low volumes in a sample; and to screen for and genotype SNPs in a sample. The highly orthogonal universal sequences may also be used as universal capture probes to immobilize amplification products produced by PCR and other gene amplification procedures for further analysis.

In one embodiment of the invention, the highly orthogonal universal sequences of the present invention are used in singleplex or multiplex bDNA assays to quantitate mRNA levels in a sample. Use of the highly orthogonal universal sequences for quantifying cytokine mRNA is described in Example 3 and shown in FIG. 2. In this Example, mRNA of nine cytokines was quantitated in a multiplex bDNA assay. The results of Example 3 show the accuracy of the highly orthogonal universal probes of the present invention in quantitating mRNA and in particular demonstrate the negligible degree of cross-reactivity between targets when the highly orthogonal universal sequences of the present invention are used in multiplex bDNA assays to quantitate target mRNA. It is understood of course, that in a singleplex bDNA cytokine assay, the mRNA of only one cytokine would be screened for and quantitated.

The use of the highly orthogonal universal sequences in bDNA assays for quantitating mRNA is not limited to the quantitation of cytokine mRNA; the highly orthogonal sequences may be used in bDNA assays to quantify mRNA from any sample. For example, the bDNA assays as described herein may be used on samples, such as cells, blood, tissue, etc., in order to quantitate transcription levels of specific genes. The use of the bDNA assay using the highly orthogonal probes in this way is widespread. For example, the quantitation of mRNA is used in clinical diagnostics to quantify the regulation and expression of drug resistance markers in tumor cells, to monitor responses to chemotherapy, to measure the biodistribution and transcription of gene-encoded therapeutics, to provide a molecular assessment of tumor stage, to detect circulating tumor cells in cancer patients, and to detect bacterial and viral pathogens.

In addition to using highly orthogonal sequences in bDNA assays to quantitate mRNA levels, the highly orthogonal sequences may also be used as probes in bDNA assays to measure changes in the amount of a gene in a sample, such as when gene amplifications or deletions occur. Within the context of the present invention, the highly orthogonal universal sequences may be used in singleplex assays to measure for amplification or deletion of copies of a single gene in a sample or they may be used in multiplex assays to measure for amplification or deletion of multiple genes in a sample. The gene or genes to be measured may be associated with any disease state. For purposes of illustration, when the disease state is cancer, the highly orthogonal universal sequences may be used to determine if extra copies of a cancerous gene are present in a tumor sample, thus indicating that the tumor may be malignant, or if fewer copies of gene are present in a previously cancerous sample, thus, indicating that the cancer is in remission. Cancer-causing genes are known to those of skill in the art and include, without limitation, such genes as the p53 oncogene and the Her-2/neu gene, whose detection in abnormally high copies has been associated with the rapid growth of breast cancer tumors. A database of cancer-causing genes is published on the Internet by the Office of Cancer Genomics of the National Cancer Institute at www3.cancer.gov/ocg/.

In a further embodiment of the invention, the highly orthogonal six-base universal sequences of the present invention are used in bDNA assays to detect DNA viruses and retroviruses having low viral load. Such DNA viruses include, without limitation, bovine and human papilloma viruses ("BPV" and "HPV," respectively); polyoma viruses, such as, for example, simian virus 40 ("SV 40"), and human polyoma virus; adenoviruses; herpesviruses, such as, for example, Epstein-Barr virus ("EBV"), human cytomegalovirus ("CMV"), herpes simplex virus ("HSV"); and the hepatitis viruses hepatitis A, B, C, and D ("HAV," "HBV," "HCV," and "HDV"). It is to be understood by those of ordinary skill in the art that although HBV is a DNA virus, it behaves more similarly to a retrovirus in that it undergoes reverse transcription. Thus, with HBV, viral DNA is transcribed into RNA for the manufacture of viral proteins and for genome replication and subsequently, the genomic RNA is transcribed back into genomic DNA. Retroviruses that may be identified by using the highly orthogonal universal sequences of the present invention in a bDNA assay include, without limitation, oncoviruses, such as, for example, murine leukemia virus ("MLV"), bovine leukemia virus ("BLV"), and human T-cell lymphotropic virus ("HTLV"); and lentiviruses, such as, for example, human immunodeficiency virus ("HIV"). As one example, a bDNA assay using the highly orthogonal sequences can detect HIV viral loads that are less than 50 molecules/mL of HIV RNA. As noted previously, the highly orthogonal universal sequences described herein significantly improve the sensitivity of viral and retroviral quantitation assays by minimizing the analyte cross-reactivity that was prevalent in prior assays (see, Example 4 and FIGS. 3A and 3B).

In yet another embodiment of the invention, the highly orthogonal universal sequences of the present invention are used in a bDNA assay in either singleplex or multiplex format to screen for and genotype SNPs in a sample. An example of multiplexed SNP genotyping is described in Iannone et al., supra at 132. Iannone et al. uses an oligonucleotide ligation assay ("OLA") to identify SNPs in a genomic sample. In OLA, two oligonucleotide probes are hybridized to target DNA such that the 3' end of one oligonucleotide is immediately adjacent to the 5' end of a second probe. If the two oligonucleotide probes are perfectly base-paired to the target DNA, DNA ligase is able to covalently link the two probes.

The orthogonal sequences of the present invention have use in SNP genotyping in that they may be used to design the capture probes that are used to hybridize both to the genomic targets amplified by PCR and to complementary DNA sequences that have been coupled to microspheres. It is to be understood that the highly orthogonal universal sequences of the present invention may be used in singleplex SNP genotyping assays as well as in multiplex SNP genotyping assays.

In still another embodiment of the invention, the highly orthogonal sequences of the present invention The highly orthogonal universal sequences may also be used as universal capture probes in nucleic acid assays in general where it is useful to selectively bind assay components to a substrate in a way that facilitates their further analysis during the procedure. Within the context of target amplification using PCR, the nucleic acid analyte of interest is isolated from the sample and amplified using the PCR procedure described previously. The highly orthogonal universal sequences are used to selectively capture complementary sequences and immobilize the amplicons to separate and unique solid phase binding surfaces. One member of each PCR primer pair is synthesized to contain the orthogonal capture sequence at it 5' end. Amplicons thus produced can be captured to different solid phases each derivitized with the appropriate complementary sequence. Following the PCR amplification procedure, amplicons produced are captured to unique solid phases via hybridization of the universal orthogonal sequence pairs; the capture of the amplicons may occur at temperatures ranging from 37 to 55° C. Due to the highly orthogonal nature of the claimed universal sequences, cross-reactivity between the universal nucleotide sequences and the primary or secondary structures inherent in target amplification products is minimized.

It is to be understood that while the invention has been described in conjunction with the preferred specific embodiments set forth herein, that the foregoing description as well as the examples that follow, are intended to illustrate and not limit the scope of the invention. It should be understood by those skilled in the art that various changes may be made and equivalents may be substituted without departing from the scope of the invention, and further that other aspects, advantages and modifications will be apparent to those skilled in the art to which the invention pertains.

All patents, publications, and other published documents mentioned or referred to both supra and infra are incorporated by reference herein in their entireties.

EXPERIMENTAL APPLICATION OF THE INVENTION

Unless otherwise indicated, the practice of the present invention uses conventional techniques of synthetic organic chemistry, biochemistry, molecular biology, and the like, which are within the skill of those in the art. Such techniques are explained fully in the literature. See e.g., Sambrook, et al., MOLECULAR CLONING: A LABORATORY MANUAL, $2^{nd}$ edition (1989); OLIGONUCLEOTIDE SYNTHESIS (M. J. Gait, ed., 1984); THE PRACTICE OF PEPTIDE SYNTHESIS (M. Bodanszky and A. Bodanszky, $2^{nd}$ ed., Springer-Verlag, New York, N.Y., 1994); NUCLEIC ACID HYBRIDIZATION (B. D. Haines & S. J. Higgins, eds., 1984); and METHODS IN ENZYMOLOGY (Academic Press, Inc.).

In the following examples, it is to be understood that while efforts have been made to ensure the accuracy of the experimental parameters (e.g., amounts, temperature, etc.), some experimental error and deviation should be taken into account when reproducing the experiments set forth below. Unless otherwise indicated, temperature values are in degrees C, pressure values are at or near atmospheric pressure. Additionally, unless otherwise indicated, all reagents were obtained commercially, all solvents were purchased as HPLC grade, and all reactions were conducted under an inert argon atmosphere. Oligonucleotides used in the examples that follow were synthesized by standard phosphoramidite chemistry.

Melting points in the following examples were determined using a thermostatted cell in a UV spectrophotometer. Plotting temperature versus absorbance, an S-shaped curve with two plateaus is observed. The absorbance reading halfway between the plateaus corresponds to Tm.

Example 1

Generating Orthogonal Universal Sequences with Six-Base Code and No More than 3-mer Interactions The following procedure was used to generate eight orthogonal sequences with six-base code having no more than 3-mer interactions between the orthogonal sequences including all complements.

One hundred random 20-mer System8 sequences were generated from a pool of 128 tetramers with iso-G and iso-C bases at the fourth positions. Out of these 100 sequences, 36 sequences were selected based on a 65% to 70% G/C content (including iso-G and iso-C). The 36 sequences were further reduced to 16 sequences by removing sequences with biased base compositions (compositions that are high on some bases and low on others). An additional isobase (either iso-G or iso-C with an attempt to balance the two bases within the particular sequence) was then added to the 5' end of each of the 16 sequences (the "orthogonal sequences").

The sixteen orthogonal sequences were converted back to their natural form (iso-G to G and iso-C to C) before using the Single Probe Comparison function of the bDNA beta program to screen for cross hybridization. See, S. Bushnell et al., BIOINFORMATICS 15(5):348-355 (1999). Within the program, the weighting factors for G/C and A/T were set to one in order to indicate the total number of x-mer interactions.

The number of x-mer interactions of the 16 orthogonal sequences were calculated manually by comparing the following sequences: (a) the 16 orthogonal sequences with eight System8 sequences and their complements; (b) the 16 orthogonal sequences with themselves; and (c) the 16 orthogonal sequences with the complements of the 16 orthogonal sequences. Due to the large number of interactions in short 3-mer and 4-mer tandems, 5mer interactions were chosen for manual examination of the sequences. A total of sixty-eight 5-mer interactions were manually aligned between the 16 orthogonal sequences and eight System8 sequences. Four of the 16 orthogonal sequences were removed from the pool due to strong interactions that could not be eliminated. Eight of the remaining orthogonal sequences were modified from their original form by swapping the G and C with iso-G and iso-C, respectively, in order to reduce the interactions at (a), (b), and (c) to at most 3-mers without generating a stretch of longer than five natural bases. Since the interactions were predicted for natural Watson-Crick base pairing, the calculated x-mer interactions were rendered insignificant upon reincorporation of the isobases back into the sequences.

Subsequent runs of aligning, eliminating, and modifying were reiterated on the (b) and (c) interactions as described above. Other sequence modifications used to achieve no more than 3-mer interactions included the following: (i) increasing isobase content by converting some G/C to iso-G and iso-C;

and (ii) reducing the size to 20-mer by deleting one of the terminal isobases. A total of five reiterations were performed to result in eight new universal orthogonal sequences with at most 3-mer interactions among themselves and the System8 sequences including all complements.

Example 2

Production of Optimized Orthogonal Universal Sequences

Multiple optimized CPs were designed from a 20-mer sequence comprised of a six-base code consisting of four natural bases and the two non-natural bases, iso-G and iso-C. FIG. 1A shows a generic structure of the initial 20-mer sequences of the present invention, which were composed of tetramer units consisting of four natural bases arranged in no specific order separated by a single iso-G or iso-C base. To produce probes from the initial 20-mer sequences, the initial sequences were screened according to the procedure set forth in Example 1 in order to produce 33 CPs and 33 CEs having approximately 50% G/C composition and melting points near 80° C. The resulting sequences were used to design a sixplex cytokine assay panel. Because the probes demonstrated some cross-reactivity in the cytokine assay, the probes were further optimized for minimal cross-reactivity by constraining the melting temperature of the probes near 85° C. The optimal set of probes that resulted from the screening and testing are described by the formula of FIG. 1B and are represented in Table 1. When the sequences of Table 1 were incorporated into an elevenplex cytokine bDNA assay panel, the sequences exhibited highly orthogonal behavior, i.e., little to no cross-reactivity. The following abbreviations are used in the tables that follow:

F=iso-C,

J=iso-G,

Tm=the melting temperature is the temperature in ° C. at which 50% of an oligonucleotide probe is annealed to its complement, Td=the disassociation temperature is the temperature in ° C. at which 50% of an oligonucleotide probe is annealed to its membrane-bound complement, and Bck=background.

TABLE 1

ORTHOGONAL UNIVERSAL SEQUENCES

| NAME | CP SEQUENCES (5'-3') | NAME | CE SEQUENCES (5'-3') | LENGTH | Tm | Td |
|---|---|---|---|---|---|---|
| CP1 | TFCCJACJTFGFTGAFTCGJ (SEQ ID NO. 1) | CE1 | FCGAJTCAJCJAFGTFGGJA (SEQ ID NO. 2) | 20 | 84.7 | 69.7 |
| CP2 | FTTAFGAGJTJAGCGFFCGCC (SEQ ID NO. 3) | CE2 | GGCGJJCGCTFAFCTCJTAAJ (SEQ ID NO. 4) | 21 | 85.0 | 72.4 |
| CP3 | JTCFCCTAFGJACAAGJCJCG (SEQ ID NO. 5) | CE3 | CGFGFCTTGTFCJTAGGJGAF (SEQ ID NO. 6) | 21 | 84.8 | 72.0 |
| CP4 | FCCGCAAFJAATGJGGJTCAF (SEQ ID NO. 7) | CE4 | JTGAFCCFCATTFJTTGCGGJ (SEQ ID NO. 8) | 21 | 85.1 | 70.0 |
| CP5 | GATAJJATFGTCFAGJFGCCJ (SEQ ID NO. 9) | CE5 | FGGCJFCTJGACJATFFTATC (SEQ ID NO. 10) | 21 | 85.0 | 70.2 |
| CP6 | GGCAFGJTFFTTJCCAFCTTJ (SEQ ID NO. 11) | CE6 | FAAGJTGGFAAJJAFCJTGCC (SEQ ID NO. 12) | 21 | 85.6 | 70.2 |
| CP7 | GCJATJCATCFGAFGTJCCTF (SEQ ID NO. 13) | CE7 | JAGGFACJTCJGATGFATFGC (SEQ ID NO. 14) | 21 | 84.2 | 73.0 |
| CP8 | CACFAGJGTJCGTTJCCJATF (SEQ ID NO. 15) | CE8 | JATFGGFAACGFACFCTJGTG (SEQ ID NO. 16) | 21 | 84.0 | 70.8 |
| CP9 | CJTTGGFTCTJTFCAJCJTGCA (SEQ ID NO. 17) | CE9 | TGCAFGFTGJAFAGAJCCAAFG (SEQ ID NO. 18) | 22 | 85.0 | 73.4 |
| CP10 | ACTCFAAJGGFTCCJTGJATCFTC (SEQ ID NO. 19) | CE10 | GAJGATFCAFGGAJCCFTTJGAGT (SEQ ID NO. 20) | 24 | 85.2 | 76.5 |
| CP11 | FCGJTAFATCJCAFTCJAGTGFT (SEQ ID NO. 21) | CE11 | AJCACTFGAJTGFGATJTAFCGJ (SEQ ID NO. 22) | 23 | 84.9 | 74.9 |
| CP12 | ACAFTTCJCTJAGAGFGTJGCCG (SEQ ID NO. 23) | CE12 | CGGCFACJCTCTFAGFGAAJTGT (SEQ ID NO. 24) | 23 | 84.5 | 76.7 |
| CP13 | GCAJCCTTJCFTGAJCAFGAJC (SEQ ID NO. 25) | CE13 | GFTCJTGFTCAJGFAAGGFTGC (SEQ ID NO. 26) | 22 | 85.3 | 75.6 |
| CP14 | CJCFACTJTGFAGFCAGAJTGC (SEQ ID NO. 27) | CE14 | GCAFTCTGJCTJCAFAGTJGFG (SEQ ID NO. 28) | 22 | 84.6 | 74.6 |
| CP15 | CTFCTGJGTFTGJTCCAJTGTCFC (SEQ ID NO. 29) | CE15 | GJGACAFTGGAFCAJACFCAGJAG (SEQ ID NO. 30) | 24 | 84.1 | 76.0 |
| CP16 | GGTTJGAAFCJAJTGCFTCGCTC (SEQ ID NO. 31) | CE16 | GAGCGAJGCAFTFGJTTCFAACG (SEQ ID NO. 32) | 23 | 83.9 | 76.1 |

TABLE 1-continued

ORTHOGONAL UNIVERSAL SEQUENCES

| NAME | CP SEQUENCES (5'-3') | NAME | CE SEQUENCES (5'-3') | LENGTH | Tm | Td |
|---|---|---|---|---|---|---|
| CP17 | GTJTCGFACCAFAJCTFGGTATJC (SEQ ID NO. 33) | CE17 | GFATACCJAGFTJTGGTJCGAFAC (SEQ ID NO. 34) | 24 | 84.9 | 78.6 |
| CP18 | GTJTGFCACAJAFTCGFTTGCFTG (SEQ ID NO. 35) | CE18 | CAJGCAAJCGAJTFTGTGJCAFAC (SEQ ID NO. 36) | 24 | 85.1 | 77.3 |
| CP19 | TCAJAGFCACJTGAGJGAFCTCJT (SEQ ID NO. 37) | CE19 | AFGAGJTCFGTCAFGTGJCTFTGA (SEQ ID NO. 38) | 24 | 85.3 | 77.8 |
| CP20 | GJGTCAFCGJATFTCAGFTCAJCT (SEQ ID NO. 39) | CE20 | AGFTGAJCTGAJATFCGJTGACFC (SEQ ID NO. 40) | 24 | 84.2 | 77.2 |
| CP21 | CAJGAJCTACFGACAFAGAGFTGFC (SEQ ID NO. 41) | CE21 | GJCAJCTCTJTGTCJGTAGFTCFTG (SEQ ID NO. 42) | 25 | 85.0 | 78.8 |
| CP22 | GFGTTFACTCJCFAAGJTTCFAA (SEQ ID NO. 43) | CE22 | TTJGAAFCTTJGFGAGTJAACJC (SEQ ID NO. 44) | 23 | 84.6 | 74.3 |
| CP23 | TFCGTFAGGAJATCCJACAFGFA (SEQ ID NO. 45) | CE23 | TJCJTGTFGGATFTCCTJACGJA (SEQ ID NO. 46) | 23 | 85.5 | 75.5 |
| CP24 | CCJAAGFGTFTGFCTGTJAGTJC (SEQ ID NO. 47) | CE24 | GFACTFACAGJCAJACJCTTFGG (SEQ ID NO. 48) | 23 | 85.2 | 76.1 |
| CP25 | GFGTTCJAAGCFTGACFGAJTTJ (SEQ ID NO. 49) | CE25 | FAAFTCJGTCAJGCTTFGAACJC (SEQ ID NO. 50) | 23 | 84.4 | 75.0 |
| CP26 | ACFTJCTTGFGTCAJACCTJGAJC (SEQ ID NO. 51) | CE26 | GFTCFAGGTFTGACJCAAGFAJGT (SEQ ID NO. 52) | 24 | 85.2 | 78.1 |
| CP27 | GFAGGTJCCAJTCGFTAFGATGJ (SEQ ID NO. 53) | CE27 | FCATCJTAJCGAFTGGFACCTJC (SEQ ID NO. 54) | 23 | 85.0 | 75.5 |
| CP28 | TCTGFGTGAFACJTGJTCTFGGCT (SEQ ID NO. 55) | CE28 | AGCCJAGAFCAFGTJTCACJCAGA (SEQ ID NO. 56) | 24 | 84.7 | 79.2 |
| CP29 | AFGTGTFTTFCJCTCJATGGFAA (SEQ ID NO. 57) | CE29 | TTJCCATFGAGFGJAAJACACJT (SEQ ID NO. 58) | 23 | 84.9 | 75.0 |
| CP30 | CJCTJTCJCAGTJTAGFCTGCFT (SEQ ID NO. 59) | CE30 | AJGCAGJCTAFACTGFGAFAGFG (SEQ ID NO. 60) | 23 | 85.0 | 76.2 |
| CP31 | GFTGTCJCTACJTGTGFGFTTTGC (SEQ ID NO. 61) | CE31 | GCAAAJCJCACAFGTAGFGACAJC (SEQ ID NO. 62) | 24 | 85.1 | 80.0 |
| CP32 | CGAAFGCTFTJAGGTFAFAGCJTC (SEQ ID NO. 63) | CE32 | GAFGCTJTJACCTFAJAGCJTTCG (SEQ ID NO. 64) | 24 | 84.4 | 78.0 |
| CP33 | GTJCTCFAGAJGCTJATGFCGF (SEQ ID NO. 65) | CE33 | JCGJCATFAGCFTCTJGAGFAC (SEQ ID NO. 66) | 22 | 85.0 | 75.0 |

Example 3

Specificity of Multiplex Cytokine mRNA Assay

Figure 2:
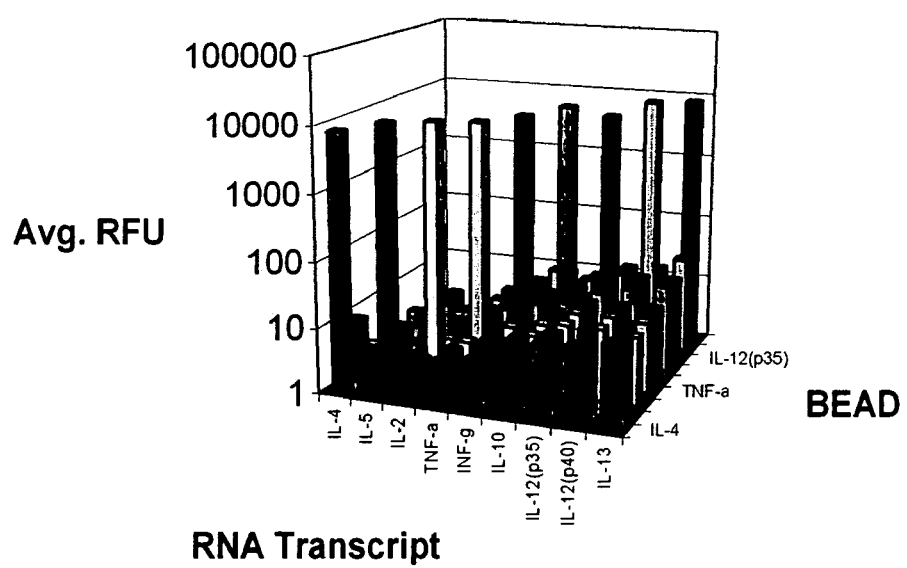
FIG. 2 is a graph showing the use of the orthogonal sequences of the claimed invention in a nineplex cytokine mRNA quantitation assay using bDNA.

The Universal Orthogonal Sequences CP1-CP9 and CE1-CE9 (SEQ ID Nos. 1-22) from Table 1 were used in a multiplex cytokine mRNA quantitation assay using bDNA design principles and the Luminex® suspension array technology for readout. Table 2 shows the performance of the multiplex mRNA assay on approximately 60,000,000 molecules of target for nine cytokines using CP1-CP9 and CE1-CE9. In this experiment, the complete bDNA assay was run for each cytokine. As demonstrated in Table 2, very strong RFU signals were seen on the expected beads and crosshybridization of the selected universal sequences was negligible when compared to the background signal of the assay beads. FIG. 2 shows the results of this assay in a three-dimensional bar graph.

TABLE 2

| | IL-4 | IL-5 | IL-2 | TNF-α | INF-γ | IL-10 | IL-12 [p35] | IL-12 [p40] | IL-13 |
|---|---|---|---|---|---|---|---|---|---|
| IL-4 | 8238 | 5 | 5 | 4 | 6 | 12 | 13 | 15 | 18 |
| IL-5 | 9 | 9623 | 3 | 5 | 7 | 10 | 13 | 17 | 23 |
| IL-2 | 3 | 1 | 8721 | 4 | 5 | 7 | 13 | 13 | 12 |
| TNF-α | 2 | 1 | 3 | 7568 | 6 | 7 | 13 | 13 | 12 |
| INF-γ | 2 | 1 | 3 | 6 | 8213 | 8 | 13 | 13 | 13 |
| IL-10 | 3 | 5 | 3 | 5 | 7 | 10009 | 13 | 17 | 21 |
| IL-12 [p35] | 2 | 2 | 3 | 5 | 7 | 12 | 6258 | 19 | 19 |

TABLE 2-continued

| | IL-4 | IL-5 | IL-2 | TNF-α | INF-γ | IL-10 | IL-12 [p35] | IL-12 [p40] | IL-13 |
|---|---|---|---|---|---|---|---|---|---|
| IL-12 [p40] | 2 | 1 | 3 | 7 | 12 | 10 | 13 | 9285 | 31 |
| IL-13 | 2 | 1 | 3 | 5 | 8 | 8 | 13 | 14 | 8515 |
| BEAD BKG | 2 | 1 | 3 | 5 | 5 | 8 | 13 | 13 | 12 |

Example 4

Cross Hybridization of the Universal Orthogonal Sequences Versus the ZipCode Sequences The first eleven Orthogonal Universal Sequences of Table 1, i.e., CP1-CP11 and CE1-CE11 (SEQ ID NOS. 1-22) were compared with the ZipCode sequences described by Iannone et al., supra; the ZipCode sequences are a set of universal sequences based entirely on natural bases. This experiment was designed to determine if the Universal Orthogonal Sequences containing the non-natural iso-C and iso-G bases are demonstrably superior in function to sequences that contain all natural bases. The ZipCode sequences used in this comparative analysis are set forth in Table 3.

TABLE 3

ZIPCODES USED FOR COMPARISON

| NAME | CP SEQUENCES (5'-3') | NAME | CE SEQUENCES (5'-3') | LENGTH | Tm | Td |
|---|---|---|---|---|---|---|
| ZCP03 | GACATTCGCGATCGCCGCCCGCTTT (SEQ ID NO. 67) | ZCE03 | AAAGCGGGCGGCGATCGCGAATGTC (SEQ ID NO. 68) | 25 | 77 | 77 |
| ZCP06 | CACCGCCAGCTCGGCTTCGAGTTCG (SEQ ID NO. 69) | ZCE06 | CGAACTCGAAGCCGAGCTGGCGGTG (SEQ ID NO. 70) | 25 | 74 | 75 |
| ZCP10 | GAACCTTTCGCTTCACCGGCCGATC (SEQ ID NO. 71) | ZCE10 | GATCGGCCGGTGAAGCGAAAGGTTC (SEQ ID NO. 72) | 25 | 71 | 74 |
| ZCP24 | CCGGCTTTGAACTGCTCACCGATCT (SEQ ID NO. 73) | ZCE24 | AGATCGGTGAGCAGTTCAAAGCCGG (SEQ ID NO. 74) | 25 | 68 | 71 |
| ZCP44 | AGCAGCAGTGACAATGCCACCGCCG (SEQ ID NO. 75) | ZCE44 | CGGCGGTGGCATTGTCACTGCTGCT (SEQ ID NO. 76) | 25 | 73 | 75 |
| ZCP46 | TCGCCCGCGGACACCGAGAATTCGA (SEQ ID NO. 77) | ZCE46 | TCGAATTCTCGGTGTCCGCGGGCGA (SEQ ID NO. 78) | 25 | 76 | 76 |
| ZCP56 | CACCACCAGTGCCGCTACCACAACG (SEQ ID NO. 79) | ZCE56 | CGTTGTGGTAGCGGCACTGGTGGTG (SEQ ID NO. 80) | 25 | 70 | 73 |
| ZCP59 | CGGCGGTCTTCACGCTCAACAGCAG (SEQ ID NO. 81) | ZCE59 | CTGCTGTTGAGCGTGAAGACCGCCG (SEQ ID NO. 82) | 25 | 71 | 74 |
| ZCP64 | AGCCGCGAACAGCACGATCGACCGG (SEQ ID NO. 83) | ZCE64 | CCGGTCGATCGTGGTGTTCGCGGCT (SEQ ID NO. 84) | 25 | 76 | 76 |
| ZCP66 | TACCGGCGGCAGCACCAGCGGTAAC (SEQ ID NO. 85) | ZCE66 | GTTACCGCTGGTGCTGCCGCCGGTA (SEQ ID NO. 86) | 25 | 74 | 76 |

Figure 3A:
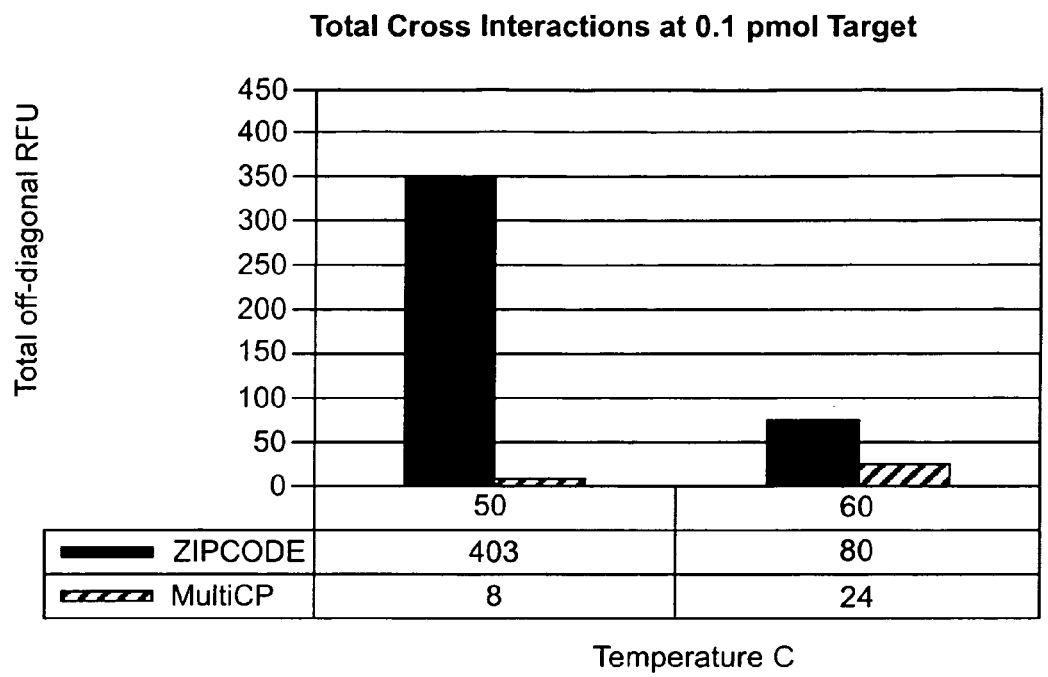
FIG. 3A is a comparative graph showing cross-interactions of the orthogonal sequences of the present invention versus ZipCode sequences at 0.1 pmol target.
Figure 3B:
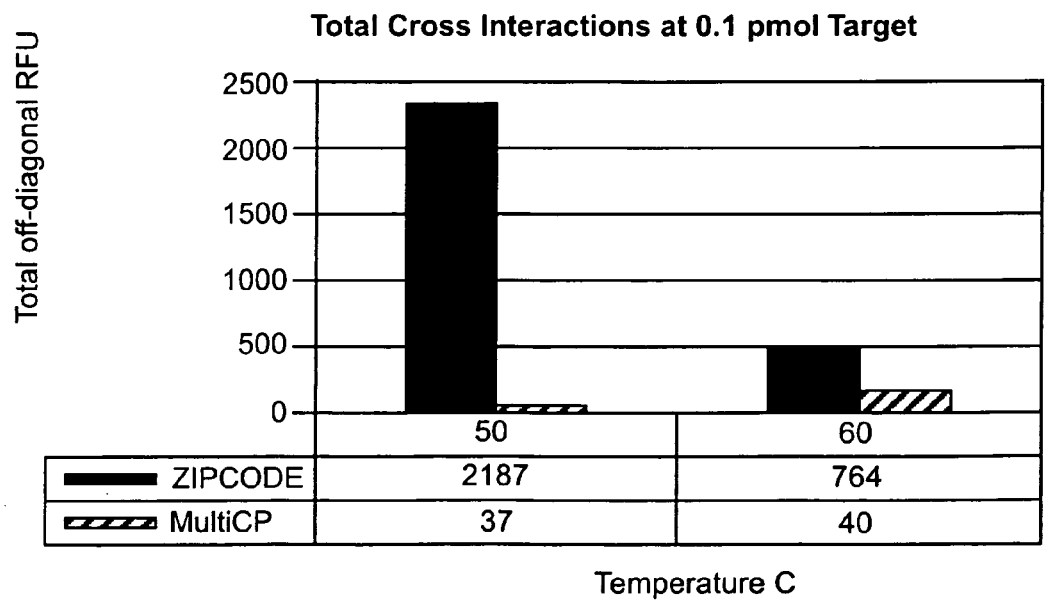
FIG. 3B is a comparative graph showing cross-interactions of the orthogonal sequences of the present invention versus ZipCode sequences at 1 pmol target.

To determine the superiority of universal sequences containing iso-G and iso-C residues over sequences based entirely on natural bases, the ten pairs of ZipCode sequences from Table 3 and randomly selected Orthogonal Universal Sequences from Table 1 were used to construct two 10×10 matrices for hybridization. A two-piece hybridization assay was performed with the capture probes bound to Luminex® beads and biotinylated complementary capture extender probes. The reaction used approximately 1000 Luminex® beads per capture sequence type, which is equivalent to approximately 1-2 fentomoles of DNA binding capacity. Labeling was performed with a streptavidin phycoerythrin conjugate after the hybridization step; in this way, only non-specific interactions between the orthogonal pairs was observed. As shown in FIGS. 3A and 3b, a significant amount of cross interactions were observed between non-complementary sequence pairs in ZipCode, while cross interactions between noncomplementary sequences pairs of the orthogonal sequences of the present invention were negligible under identical conditions. FIG. 3A depicts the results of the experiment at 0.1 pmol target and FIG. 3B depicts the results of the experiment at 1 pmol target. The amount of target was the amount of free probe in solution with 0.1 pmol and 1.0 pmol representing a large molar excess over the amount of capture probe covalently immobilized onto the bead.

We claim:

1. A sequence prepared from six nucleotide bases, wherein the six nucleotide bases are comprised of four natural bases selected from the group consisting of guanosine (G), cytosine (C), adenosine (A), thymidine (T), and uracil (U) and two non-natural bases selected from isoguanosine (isoG) and isocytosine (isoC), wherein for the length of the sequence, one to five of the natural bases, arranged in no specific order, are separated by isoC or isoG, wherein at least 65% of the sequence is comprised of G, C, isoC, and isoG and the sequence has a melting temperature Tm of approximately 80-85° C., wherein the number of isoG and isoC bases in the sequence is balanced and the sequence has at least one incidence of five natural bases separated by isoC or isoG.

2. The sequence of claim 1, wherein the sequence has a Tm of approximately 85° C.

3. The sequence of claim 1, wherein the sequence ranges in length from 20-25 bases.

4. A method of immobilizing a target amplification product to a substrate comprising attaching the sequence of claim 1 to a substrate, wherein the sequence is used as a capture probe to immobilize the target amplification product to the substrate.

5. The method of claim 4, wherein the target amplification product is an amplicon produced by polymerase chain reaction.

6. The method of claim 5, wherein the substrate is a solid phase binding surface derivitized with a sequence complementary to the capture probe.

7. A bDNA assay performed with the sequence of claim 1.

8. The bDNA assay of claim 7, used to detect DNA viruses.

9. The bDNA assay of claim 8, wherein the DNA viruses are selected from the group consisting of bovine or human papilloma virus, polyoma virus, adenovirus, herpesvirus, and hepatitis virus.

10. The bDNA assay of claim 9, wherein the polyoma virus is selected from the group consisting of simian virus 40 and human polyoma virus.

11. The bDNA assay of claim 9, wherein the herpesvirus is selected from the group consisting of Epstein-Barr virus, human cytomegalovirus, and herpes simplex virus.

12. The bDNA assay of claim 9, wherein the hepatitis virus is selected from the group consisting of hepatitis A, hepatitis B, hepatitis C, and hepatitis D.

13. The bDNA assay of claim 7 used to detect retroviruses.

14. The bDNA assay of claim 13, wherein the retroviruses are selected from the group consisting of oncovirus and lentivirus.

15. The bDNA assay of claim 14, wherein the oncovirus is selected from the group consisting of murine leukemia virus, bovine leukemia virus, and human T-cell lymphotropic virus.

16. The bDNA assay of claim 13, wherein the lentivirus is human immunodeficiency virus (HIV).

17. The bDNA assay of claim 16, used to detect less than 50 molecules per mL of HIV.

18. The bDNA assay of claim 7, used in a singleplex assay to genotype a single nucleotide polymorphism in a sample.

19. The bDNA assay of claim 7, used in a multiplex assay to genotype multiple single nucleotide polymorphisms in a sample.

20. The bDNA assay of claim 7, used in a singleplex assay to quantify mRNA in a sample.

21. The bDNA assay of claim 7, used in a multiplex format to quantify mRNA in a sample.

22. The bDNA assay of claim 20, wherein the singleplex assay is used to quantify a single cytokine mRNA from a sample.

23. The bDNA assay of claim 21, wherein the multiplex assay is used to quantify multiple cytokine mRNAs from a sample.

24. The bDNA assay of claim 7, used in a singleplex assay to measure amplification of copies of a single gene in a sample.

25. The bDNA assay of claim 7, used in a singleplex assay to measure deletion of copies of a single gene in a sample.

26. The bDNA assay of claim 7, used in a multiplex assay to measure amplification of copies of multiple genes in a sample.

27. The bDNA assay of claim 7, used in a multiplex assay to measure deletion of copies of multiple genes in a sample.

* * * * *

SEQUENCE LISTING

<160> NUMBER OF SEQ ID NOS: 86

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (2)..(2)
<223> OTHER INFORMATION: n=isocytosine
<220> FEATURE:
<221> NAME/KEY: modified_base
<222> LOCATION: (5)..(5)
<223> OTHER INFORMATION: n=isoguanine
<220> FEATURE:
<221> NAME/KEY: modified_base
<222> LOCATION: (8)..(8)
<223> OTHER INFORMATION: N=isoguanine
<220> FEATURE:
<221> NAME/KEY: modified_base
<222> LOCATION: (10)..(10)
<223> OTHER INFORMATION: n=isocytosine
<220> FEATURE:
<221> NAME/KEY: modified_base
<222> LOCATION: (12)..(12)
<223> OTHER INFORMATION: n=isocytosine
<220> FEATURE:
<221> NAME/KEY: modified_base
<222> LOCATION: (16)..(16)
<223> OTHER INFORMATION: N=isocytosine
<220> FEATURE:
<221> NAME/KEY: modified_base
<222> LOCATION: (20)..(20)
<223> OTHER INFORMATION: n=isoguanine

<400> SEQUENCE: 1
tnccnacntn gntgantcgn                                              20

<210> SEQ ID NO 2
<211> LENGTH: 20
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (1)..(1)
<223> OTHER INFORMATION: n=isocytosine
<220> FEATURE:
<221> NAME/KEY: modified_base
<222> LOCATION: (5)..(5)
<223> OTHER INFORMATION: n=isoguanine
<220> FEATURE:
<221> NAME/KEY: modified_base
<222> LOCATION: (9)..(9)
<223> OTHER INFORMATION: n=isoguanine
<220> FEATURE:
<221> NAME/KEY: modified_base
<222> LOCATION: (11)..(11)
<223> OTHER INFORMATION: n=isogunaine
<220> FEATURE:
<221> NAME/KEY: modified_base
<222> LOCATION: (13)..(13)
<223> OTHER INFORMATION: n=isocytosine
<220> FEATURE:
<221> NAME/KEY: modified_base
<222> LOCATION: (16)..(16)
<223> OTHER INFORMATION: n=isocytosine
<220> FEATURE:
<221> NAME/KEY: modified_base
<222> LOCATION: (19)..(19)

<223> OTHER INFORMATION: n=isoguanine

<400> SEQUENCE: 2
ncgantcanc nangtnggna                                           20

<210> SEQ ID NO 3
<211> LENGTH: 21
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (1)..(1)
<223> OTHER INFORMATION: n=isocytosine
<220> FEATURE:
<221> NAME/KEY: modified_base
<222> LOCATION: (5)..(5)
<223> OTHER INFORMATION: n=isocytosine
<220> FEATURE:
<221> NAME/KEY: modified_base
<222> LOCATION: (9)..(9)
<223> OTHER INFORMATION: n=isoguanine
<220> FEATURE:
<221> NAME/KEY: modified_base
<222> LOCATION: (11)..(11)
<223> OTHER INFORMATION: n=isoguanine
<220> FEATURE:
<221> NAME/KEY: modified_base
<222> LOCATION: (16)..(16)
<223> OTHER INFORMATION: n=isocytosine
<220> FEATURE:
<221> NAME/KEY: modified_base
<222> LOCATION: (17)..(17)
<223> OTHER INFORMATION: n=isocytosine

<400> SEQUENCE: 3
nttangagnt nagcgnncgc c                                         21

<210> SEQ ID NO 4
<211> LENGTH: 21
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (5)..(5)
<223> OTHER INFORMATION: n=isoguanine
<220> FEATURE:
<221> NAME/KEY: modified_base
<222> LOCATION: (6)..(6)
<223> OTHER INFORMATION: n=isoguanine
<220> FEATURE:
<221> NAME/KEY: modified_base
<222> LOCATION: (11)..(11)
<223> OTHER INFORMATION: n=isocytosine
<220> FEATURE:
<221> NAME/KEY: modified_base
<222> LOCATION: (13)..(13)
<223> OTHER INFORMATION: n=isocytosine
<220> FEATURE:
<221> NAME/KEY: modified_base
<222> LOCATION: (17)..(17)
<223> OTHER INFORMATION: n=isoguanine
<220> FEATURE:
<221> NAME/KEY: modified_base
<222> LOCATION: (21)..(21)
<223> OTHER INFORMATION: n=isoguanine

<400> SEQUENCE: 4
ggcgnncgct nanctcntaa n                                         21

<210> SEQ ID NO 5
<211> LENGTH: 21
<212> TYPE: DNA
<213> ORGANISM: Artificial sequence
<220> FEATURE:
<223> OTHER INFORMATION: Description of Artificial Sequence: Synthetic
    orthogonal universal sequence probe
<220> FEATURE:
<221> NAME/KEY: modified_base
<222> LOCATION: (1)..(1)
<223> OTHER INFORMATION: n=isoguanine
<220> FEATURE:
<221> NAME/KEY: modified_base
<222> LOCATION: (4)..(4)
<223> OTHER INFORMATION: n=isocytosine
<220> FEATURE:
<221> NAME/KEY: modified_base
<222> LOCATION: (9)..(9)
<223> OTHER INFORMATION: n=isocytosine
<220> FEATURE:
<221> NAME/KEY: modified_base
<222> LOCATION: (11)..(11)
<223> OTHER INFORMATION: n=isoguanine
<220> FEATURE:
<221> NAME/KEY: modified_base
<222> LOCATION: (17)..(17)
<223> OTHER INFORMATION: n=isoguanine
<220> FEATURE:
<221> NAME/KEY: modified_base
<222> LOCATION: (19)..(19)
<223> OTHER INFORMATION: n=isoguanine

<400> SEQUENCE: 5
ntcncctang nacaagncnc g                                        21

<210> SEQ ID NO 6
<211> LENGTH: 21
<212> TYPE: DNA
<213> ORGANISM: Artificial sequence
<220> FEATURE:
<223> OTHER INFORMATION: Description of Artificial Sequence: Synthetic
    orthogonal universal sequence probe
<220> FEATURE:
<221> NAME/KEY: modified_base
<222> LOCATION: (3)..(3)
<223> OTHER INFORMATION: n=isocytosine
<220> FEATURE:
<221> NAME/KEY: modified_base
<222> LOCATION: (5)..(5)
<223> OTHER INFORMATION: n=isocytosine
<220> FEATURE:
<221> NAME/KEY: modified_base
<222> LOCATION: (11)..(11)
<223> OTHER INFORMATION: n=isocytosine
<220> FEATURE:
<221> NAME/KEY: modified_base
<222> LOCATION: (13)..(13)
<223> OTHER INFORMATION: n=isoguanine
<220> FEATURE:
<221> NAME/KEY: modified_base
<222> LOCATION: (18)..(18)
<223> OTHER INFORMATION: n=isoguanine
<220> FEATURE:
<221> NAME/KEY: modified_base
<222> LOCATION: (21)..(21)
<223> OTHER INFORMATION: n=isocytosine

<400> SEQUENCE: 6
cgngncttgt ncntaggnga n                                        21

<210> SEQ ID NO 7
<211> LENGTH: 21
<212> TYPE: DNA
<213> ORGANISM: Artificial sequence
<220> FEATURE:

-continued

```
<223> OTHER INFORMATION: Description of Artificial Sequence: Synthetic
      orthogonal universal sequence probe
<220> FEATURE:
<221> NAME/KEY: modified_base
<222> LOCATION: (1)..(1)
<223> OTHER INFORMATION: n=isocytosine
<220> FEATURE:
<221> NAME/KEY: modified_base
<222> LOCATION: (8)..(8)
<223> OTHER INFORMATION: n=isocytosine
<220> FEATURE:
<221> NAME/KEY: modified_base
<222> LOCATION: (9)..(9)
<223> OTHER INFORMATION: n=isoguanine
<220> FEATURE:
<221> NAME/KEY: modified_base
<222> LOCATION: (14)..(14)
<223> OTHER INFORMATION: n=isoguanine
<220> FEATURE:
<221> NAME/KEY: modified_base
<222> LOCATION: (17)..(17)
<223> OTHER INFORMATION: n=isoguanine
<220> FEATURE:
<221> NAME/KEY: modified_base
<222> LOCATION: (21)..(21)
<223> OTHER INFORMATION: n=isocytosine

<400> SEQUENCE: 7
nccgcaanna atgnggntca n                                          21

<210> SEQ ID NO 8
<211> LENGTH: 21
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (1)..(1)
<223> OTHER INFORMATION: n=isoguanine
<220> FEATURE:
<221> NAME/KEY: modified_base
<222> LOCATION: (5)..(5)
<223> OTHER INFORMATION: n=isocytosine
<220> FEATURE:
<221> NAME/KEY: modified_base
<222> LOCATION: (8)..(8)
<223> OTHER INFORMATION: n=isocytosine
<220> FEATURE:
<221> NAME/KEY: modified_base
<222> LOCATION: (13)..(13)
<223> OTHER INFORMATION: n=isocytosine
<220> FEATURE:
<221> NAME/KEY: modified_base
<222> LOCATION: (14)..(14)
<223> OTHER INFORMATION: n=isoguanine
<220> FEATURE:
<221> NAME/KEY: modified_base
<222> LOCATION: (21)..(21)
<223> OTHER INFORMATION: n=isoguanine

<400> SEQUENCE: 8
ntganccnca ttnnttgcgg n                                          21

<210> SEQ ID NO 9
<211> LENGTH: 21
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (5)..(5)
<223> OTHER INFORMATION: n=isoguanine
```

```
<220> FEATURE:
<221> NAME/KEY: modified_base
<222> LOCATION: (6)..(6)
<223> OTHER INFORMATION: n=isoguanine
<220> FEATURE:
<221> NAME/KEY: modified_base
<222> LOCATION: (9)..(9)
<223> OTHER INFORMATION: n=isocytosine
<220> FEATURE:
<221> NAME/KEY: modified_base
<222> LOCATION: (13)..(13)
<223> OTHER INFORMATION: n=isocytosine
<220> FEATURE:
<221> NAME/KEY: modified_base
<222> LOCATION: (16)..(16)
<223> OTHER INFORMATION: n=isoguanine
<220> FEATURE:
<221> NAME/KEY: modified_base
<222> LOCATION: (17)..(17)
<223> OTHER INFORMATION: n=isocytosine
<220> FEATURE:
<221> NAME/KEY: modified_base
<222> LOCATION: (21)..(21)
<223> OTHER INFORMATION: n=isoguanine

<400> SEQUENCE: 9
gatannatng tcnagnngcc n                                              21

<210> SEQ ID NO 10
<211> LENGTH: 21
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (1)..(1)
<223> OTHER INFORMATION: n=isocytosine
<220> FEATURE:
<221> NAME/KEY: modified_base
<222> LOCATION: (5)..(5)
<223> OTHER INFORMATION: n=isoguanine
<220> FEATURE:
<221> NAME/KEY: modified_base
<222> LOCATION: (6)..(6)
<223> OTHER INFORMATION: n=isocytosine
<220> FEATURE:
<221> NAME/KEY: modified_base
<222> LOCATION: (9)..(9)
<223> OTHER INFORMATION: n=isoguanine
<220> FEATURE:
<221> NAME/KEY: modified_base
<222> LOCATION: (13)..(13)
<223> OTHER INFORMATION: n=isoguanine
<220> FEATURE:
<221> NAME/KEY: modified_base
<222> LOCATION: (16)..(16)
<223> OTHER INFORMATION: n=isocytosine
<220> FEATURE:
<221> NAME/KEY: modified_base
<222> LOCATION: (17)..(17)
<223> OTHER INFORMATION: n=isocytosine

<400> SEQUENCE: 10
nggcnnctng acnatnntat c                                              21

<210> SEQ ID NO 11
<211> LENGTH: 21
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
```

<222> LOCATION: (5)..(5)
<223> OTHER INFORMATION: n=isocytosine
<220> FEATURE:
<221> NAME/KEY: modified_base
<222> LOCATION: (7)..(7)
<223> OTHER INFORMATION: n=isoguanine
<220> FEATURE:
<221> NAME/KEY: modified_base
<222> LOCATION: (9)..(9)
<223> OTHER INFORMATION: n=isocytosine
<220> FEATURE:
<221> NAME/KEY: modified_base
<222> LOCATION: (10)..(10)
<223> OTHER INFORMATION: n=isocytosine
<220> FEATURE:
<221> NAME/KEY: modified_base
<222> LOCATION: (13)..(13)
<223> OTHER INFORMATION: n=isoguanine
<220> FEATURE:
<221> NAME/KEY: modified_base
<222> LOCATION: (17)..(17)
<223> OTHER INFORMATION: n=isocytosine
<220> FEATURE:
<221> NAME/KEY: modified_base
<222> LOCATION: (21)..(21)
<223> OTHER INFORMATION: n=isoguanine

<400> SEQUENCE: 11
ggcangntnn ttnccanctt n                                     21

<210> SEQ ID NO 12
<211> LENGTH: 21
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (1)..(1)
<223> OTHER INFORMATION: n=isocytosine
<220> FEATURE:
<221> NAME/KEY: modified_base
<222> LOCATION: (5)..(5)
<223> OTHER INFORMATION: n=isoguanine
<220> FEATURE:
<221> NAME/KEY: modified_base
<222> LOCATION: (9)..(9)
<223> OTHER INFORMATION: n=isocytosine
<220> FEATURE:
<221> NAME/KEY: modified_base
<222> LOCATION: (12)..(12)
<223> OTHER INFORMATION: n=isoguanine
<220> FEATURE:
<221> NAME/KEY: modified_base
<222> LOCATION: (13)..(13)
<223> OTHER INFORMATION: n=isoguanine
<220> FEATURE:
<221> NAME/KEY: modified_base
<222> LOCATION: (15)..(15)
<223> OTHER INFORMATION: n=isocytosine
<220> FEATURE:
<221> NAME/KEY: modified_base
<222> LOCATION: (17)..(17)
<223> OTHER INFORMATION: n=isoguanine

<400> SEQUENCE: 12
naagntggna annancntgc c                                     21

<210> SEQ ID NO 13
<211> LENGTH: 21
<212> TYPE: DNA
<213> ORGANISM: Artificial sequence
<220> FEATURE:
<223> OTHER INFORMATION: Description of Artificial Sequence: Synthetic
      orthogonal universal sequence probe -continued

```
<220> FEATURE:
<221> NAME/KEY: modified_base
<222> LOCATION: (3)..(3)
<223> OTHER INFORMATION: n=isoguanine
<220> FEATURE:
<221> NAME/KEY: modified_base
<222> LOCATION: (6)..(6)
<223> OTHER INFORMATION: n=isoguanine
<220> FEATURE:
<221> NAME/KEY: modified_base
<222> LOCATION: (11)..(11)
<223> OTHER INFORMATION: n=isocytosine
<220> FEATURE:
<221> NAME/KEY: modified_base
<222> LOCATION: (14)..(14)
<223> OTHER INFORMATION: n=isocytosine
<220> FEATURE:
<221> NAME/KEY: modified_base
<222> LOCATION: (17)..(17)
<223> OTHER INFORMATION: n=isoguanine
<220> FEATURE:
<221> NAME/KEY: modified_base
<222> LOCATION: (21)..(21)
<223> OTHER INFORMATION: n=isocytosine

<400> SEQUENCE: 13
gcnatncatc ngangtncct n                                              21

<210> SEQ ID NO 14
<211> LENGTH: 21
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (1)..(1)
<223> OTHER INFORMATION: n=isoguanine
<220> FEATURE:
<221> NAME/KEY: modified_base
<222> LOCATION: (5)..(5)
<223> OTHER INFORMATION: n=isocytosine
<220> FEATURE:
<221> NAME/KEY: modified_base
<222> LOCATION: (8)..(8)
<223> OTHER INFORMATION: n=isoguanine
<220> FEATURE:
<221> NAME/KEY: modified_base
<222> LOCATION: (11)..(11)
<223> OTHER INFORMATION: n=isoguanine
<220> FEATURE:
<221> NAME/KEY: modified_base
<222> LOCATION: (16)..(16)
<223> OTHER INFORMATION: n=isocytosine
<220> FEATURE:
<221> NAME/KEY: modified_base
<222> LOCATION: (19)..(19)
<223> OTHER INFORMATION: n=isocytosine

<400> SEQUENCE: 14
naggnacntc ngatgnatng c                                              21

<210> SEQ ID NO 15
<211> LENGTH: 21
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (4)..(4)
<223> OTHER INFORMATION: n=isocytosine
<220> FEATURE:
<221> NAME/KEY: modified_base
```

```
<222> LOCATION: (7)..(7)
<223> OTHER INFORMATION: n=isoguanine
<220> FEATURE:
<221> NAME/KEY: modified_base
<222> LOCATION: (10)..(10)
<223> OTHER INFORMATION: n=isoguanine
<220> FEATURE:
<221> NAME/KEY: modified_base
<222> LOCATION: (15)..(15)
<223> OTHER INFORMATION: n=isoguanine
<220> FEATURE:
<221> NAME/KEY: modified_base
<222> LOCATION: (18)..(18)
<223> OTHER INFORMATION: n=isoguanine
<220> FEATURE:
<221> NAME/KEY: modified_base
<222> LOCATION: (21)..(21)
<223> OTHER INFORMATION: n=isocytosine

<400> SEQUENCE: 15
cacnagngtn cgttnccnat n                                            21

<210> SEQ ID NO 16
<211> LENGTH: 21
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (1)..(1)
<223> OTHER INFORMATION: n=isoguanine
<220> FEATURE:
<221> NAME/KEY: modified_base
<222> LOCATION: (4)..(4)
<223> OTHER INFORMATION: n=isocytosine
<220> FEATURE:
<221> NAME/KEY: modified_base
<222> LOCATION: (7)..(7)
<223> OTHER INFORMATION: n=isocytosine
<220> FEATURE:
<221> NAME/KEY: modified_base
<222> LOCATION: (12)..(12)
<223> OTHER INFORMATION: n=isocytosine
<220> FEATURE:
<221> NAME/KEY: modified_base
<222> LOCATION: (15)..(15)
<223> OTHER INFORMATION: n=isocytosine
<220> FEATURE:
<221> NAME/KEY: modified_base
<222> LOCATION: (18)..(18)
<223> OTHER INFORMATION: n=isoguanine

<400> SEQUENCE: 16
natnggnaac gnacnctngt g                                            21

<210> SEQ ID NO 17
<211> LENGTH: 22
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (2)..(2)
<223> OTHER INFORMATION: n=isoguanine
<220> FEATURE:
<221> NAME/KEY: modified_base
<222> LOCATION: (7)..(7)
<223> OTHER INFORMATION: n=isocytosine
<220> FEATURE:
<221> NAME/KEY: modified_base
<222> LOCATION: (11)..(11)
<223> OTHER INFORMATION: n=isoguanine
```

```
<220> FEATURE:
<221> NAME/KEY: modified_base
<222> LOCATION: (13)..(13)
<223> OTHER INFORMATION: n=isocytosine
<220> FEATURE:
<221> NAME/KEY: modified_base
<222> LOCATION: (16)..(16)
<223> OTHER INFORMATION: n=isoguanine
<220> FEATURE:
<221> NAME/KEY: modified_base
<222> LOCATION: (18)..(18)
<223> OTHER INFORMATION: n=isoguanine

<400> SEQUENCE: 17
cnttggntct ntncancntg ca                                             22

<210> SEQ ID NO 18
<211> LENGTH: 22
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (5)..(5)
<223> OTHER INFORMATION: n=isocytosine
<220> FEATURE:
<221> NAME/KEY: modified_base
<222> LOCATION: (7)..(7)
<223> OTHER INFORMATION: n=isocytosine
<220> FEATURE:
<221> NAME/KEY: modified_base
<222> LOCATION: (10)..(10)
<223> OTHER INFORMATION: n=isoguanine
<220> FEATURE:
<221> NAME/KEY: modified_base
<222> LOCATION: (12)..(12)
<223> OTHER INFORMATION: n=isoguanine
<220> FEATURE:
<221> NAME/KEY: modified_base
<222> LOCATION: (16)..(16)
<223> OTHER INFORMATION: n=isoguanine
<220> FEATURE:
<221> NAME/KEY: modified_base
<222> LOCATION: (21)..(21)
<223> OTHER INFORMATION: n=isocytosine

<400> SEQUENCE: 18
tgcangntgn anaganccaa ng                                             22

<210> SEQ ID NO 19
<211> LENGTH: 24
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (5)..(5)
<223> OTHER INFORMATION: n=isocytosine
<220> FEATURE:
<221> NAME/KEY: modified_base
<222> LOCATION: (8)..(8)
<223> OTHER INFORMATION: n=isoguanine
<220> FEATURE:
<221> NAME/KEY: modified_base
<222> LOCATION: (11)..(11)
<223> OTHER INFORMATION: n=isocytosine
<220> FEATURE:
<221> NAME/KEY: modified_base
<222> LOCATION: (15)..(15)
<223> OTHER INFORMATION: n=isoguanine
<220> FEATURE:
<221> NAME/KEY: modified_base
```

```
<222> LOCATION: (18)..(18)
<223> OTHER INFORMATION: n=isoguanine
<220> FEATURE:
<221> NAME/KEY: modified_base
<222> LOCATION: (22)..(22)
<223> OTHER INFORMATION: n=isocytosine

<400> SEQUENCE: 19
actcnaangg ntccntgnat cntc                                          24

<210> SEQ ID NO 20
<211> LENGTH: 24
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (3)..(3)
<223> OTHER INFORMATION: n=isoguanine
<220> FEATURE:
<221> NAME/KEY: modified_base
<222> LOCATION: (7)..(7)
<223> OTHER INFORMATION: n=isocytosine
<220> FEATURE:
<221> NAME/KEY: modified_base
<222> LOCATION: (10)..(10)
<223> OTHER INFORMATION: n=isocytosine
<220> FEATURE:
<221> NAME/KEY: modified_base
<222> LOCATION: (14)..(14)
<223> OTHER INFORMATION: n=isoguanine
<220> FEATURE:
<221> NAME/KEY: modified_base
<222> LOCATION: (17)..(17)
<223> OTHER INFORMATION: n=isocytosine
<220> FEATURE:
<221> NAME/KEY: modified_base
<222> LOCATION: (20)..(20)
<223> OTHER INFORMATION: n=isoguanine

<400> SEQUENCE: 20
gangatncan ggancncnttn gagt                                         24

<210> SEQ ID NO 21
<211> LENGTH: 23
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (1)..(1)
<223> OTHER INFORMATION: n=isocytosine
<220> FEATURE:
<221> NAME/KEY: modified_base
<222> LOCATION: (4)..(4)
<223> OTHER INFORMATION: n=isoguanine
<220> FEATURE:
<221> NAME/KEY: modified_base
<222> LOCATION: (7)..(7)
<223> OTHER INFORMATION: n=isocytosine
<220> FEATURE:
<221> NAME/KEY: modified_base
<222> LOCATION: (11)..(11)
<223> OTHER INFORMATION: n=isoguanine
<220> FEATURE:
<221> NAME/KEY: modified_base
<222> LOCATION: (14)..(14)
<223> OTHER INFORMATION: n=isocytosine
<220> FEATURE:
<221> NAME/KEY: modified_base
<222> LOCATION: (17)..(17)
<223> OTHER INFORMATION: n=isoguanine
```

```
<220> FEATURE:
<221> NAME/KEY: modified_base
<222> LOCATION: (22)..(22)
<223> OTHER INFORMATION: n=isocytosine

<400> SEQUENCE: 21
ncgntanatc ncantcnagt gnt                                              23

<210> SEQ ID NO 22
<211> LENGTH: 23
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (2)..(2)
<223> OTHER INFORMATION: n=isoguanine
<220> FEATURE:
<221> NAME/KEY: modified_base
<222> LOCATION: (7)..(7)
<223> OTHER INFORMATION: n=isocytosine
<220> FEATURE:
<221> NAME/KEY: modified_base
<222> LOCATION: (10)..(10)
<223> OTHER INFORMATION: n=isoguanine
<220> FEATURE:
<221> NAME/KEY: modified_base
<222> LOCATION: (13)..(13)
<223> OTHER INFORMATION: n=isocytosine
<220> FEATURE:
<221> NAME/KEY: modified_base
<222> LOCATION: (17)..(17)
<223> OTHER INFORMATION: n=isoguanine
<220> FEATURE:
<221> NAME/KEY: modified_base
<222> LOCATION: (20)..(20)
<223> OTHER INFORMATION: n=isocytosine
<220> FEATURE:
<221> NAME/KEY: modified_base
<222> LOCATION: (23)..(23)
<223> OTHER INFORMATION: n=isoguanine

<400> SEQUENCE: 22
ancactngan tgngatntan cgn                                              23

<210> SEQ ID NO 23
<211> LENGTH: 23
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (4)..(4)
<223> OTHER INFORMATION: n=isocytosine
<220> FEATURE:
<221> NAME/KEY: modified_base
<222> LOCATION: (8)..(8)
<223> OTHER INFORMATION: n=isoguanine
<220> FEATURE:
<221> NAME/KEY: modified_base
<222> LOCATION: (11)..(11)
<223> OTHER INFORMATION: n=isoguanine
<220> FEATURE:
<221> NAME/KEY: modified_base
<222> LOCATION: (16)..(16)
<223> OTHER INFORMATION: n=isocytosine
<220> FEATURE:
<221> NAME/KEY: modified_base
<222> LOCATION: (19)..(19)
<223> OTHER INFORMATION: n=isoguanine

<400> SEQUENCE: 23
```

```
acanttcnct nagagngtng ccg                                              23

<210> SEQ ID NO 24
<211> LENGTH: 23
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (5)..(5)
<223> OTHER INFORMATION: n=isocytosine
<220> FEATURE:
<221> NAME/KEY: modified_base
<222> LOCATION: (8)..(8)
<223> OTHER INFORMATION: n=isoguanine
<220> FEATURE:
<221> NAME/KEY: modified_base
<222> LOCATION: (13)..(13)
<223> OTHER INFORMATION: n=isocytosine
<220> FEATURE:
<221> NAME/KEY: modified_base
<222> LOCATION: (16)..(16)
<223> OTHER INFORMATION: n=isocytosine
<220> FEATURE:
<221> NAME/KEY: modified_base
<222> LOCATION: (20)..(20)
<223> OTHER INFORMATION: n=isoguanine

<400> SEQUENCE: 24
cggcnacnct ctnagngaan tgt                                              23

<210> SEQ ID NO 25
<211> LENGTH: 22
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (4)..(4)
<223> OTHER INFORMATION: n=isoguanine
<220> FEATURE:
<221> NAME/KEY: modified_base
<222> LOCATION: (9)..(9)
<223> OTHER INFORMATION: n=isoguanine
<220> FEATURE:
<221> NAME/KEY: modified_base
<222> LOCATION: (11)..(11)
<223> OTHER INFORMATION: n=isocytosine
<220> FEATURE:
<221> NAME/KEY: modified_base
<222> LOCATION: (15)..(15)
<223> OTHER INFORMATION: n=isoguanine
<220> FEATURE:
<221> NAME/KEY: modified_base
<222> LOCATION: (18)..(18)
<223> OTHER INFORMATION: n=isocytosine
<220> FEATURE:
<221> NAME/KEY: modified_base
<222> LOCATION: (21)..(21)
<223> OTHER INFORMATION: n=isoguanine

<400> SEQUENCE: 25
gcanccttnc ntgancanga nc                                               22

<210> SEQ ID NO 26
<211> LENGTH: 22
<212> TYPE: DNA
<213> ORGANISM: Artificial sequence
<220> FEATURE:
<223> OTHER INFORMATION: Description of Artificial Sequence: Synthetic
```

```
                                -continued orthogonal universal sequence probe
<220> FEATURE:
<221> NAME/KEY: modified_base
<222> LOCATION: (2)..(2)
<223> OTHER INFORMATION: n=isocytosine
<220> FEATURE:
<221> NAME/KEY: modified_base
<222> LOCATION: (5)..(5)
<223> OTHER INFORMATION: n=isoguanine
<220> FEATURE:
<221> NAME/KEY: modified_base
<222> LOCATION: (8)..(8)
<223> OTHER INFORMATION: n=isocytosine
<220> FEATURE:
<221> NAME/KEY: modified_base
<222> LOCATION: (12)..(12)
<223> OTHER INFORMATION: n=isoguanine
<220> FEATURE:
<221> NAME/KEY: modified_base
<222> LOCATION: (14)..(14)
<223> OTHER INFORMATION: n=isocytosine
<220> FEATURE:
<221> NAME/KEY: modified_base
<222> LOCATION: (19)..(19)
<223> OTHER INFORMATION: n=isocytosine

<400> SEQUENCE: 26
gntcntgntc angnaaggnt gc                                            22

<210> SEQ ID NO 27
<211> LENGTH: 22
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (2)..(2)
<223> OTHER INFORMATION: n=isoguanine
<220> FEATURE:
<221> NAME/KEY: modified_base
<222> LOCATION: (4)..(4)
<223> OTHER INFORMATION: n=isocytosine
<220> FEATURE:
<221> NAME/KEY: modified_base
<222> LOCATION: (8)..(8)
<223> OTHER INFORMATION: n=isoguanine
<220> FEATURE:
<221> NAME/KEY: modified_base
<222> LOCATION: (11)..(11)
<223> OTHER INFORMATION: n=isocytosine
<220> FEATURE:
<221> NAME/KEY: modified_base
<222> LOCATION: (14)..(14)
<223> OTHER INFORMATION: n=isocytosine
<220> FEATURE:
<221> NAME/KEY: modified_base
<222> LOCATION: (19)..(19)
<223> OTHER INFORMATION: n=isoguanine

<400> SEQUENCE: 27
cncnactntg nagncagant gc                                            22

<210> SEQ ID NO 28
<211> LENGTH: 22
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (4)..(4)
<223> OTHER INFORMATION: n=isocytosine
<220> FEATURE:
```

```
<221> NAME/KEY: modified_base
<222> LOCATION: (9)..(9)
<223> OTHER INFORMATION: n=isoguanine
<220> FEATURE:
<221> NAME/KEY: modified_base
<222> LOCATION: (12)..(12)
<223> OTHER INFORMATION: n=isoguanine
<220> FEATURE:
<221> NAME/KEY: modified_base
<222> LOCATION: (15)..(15)
<223> OTHER INFORMATION: n=isocytosine
<220> FEATURE:
<221> NAME/KEY: modified_base
<222> LOCATION: (19)..(19)
<223> OTHER INFORMATION: n=isoguanine
<220> FEATURE:
<221> NAME/KEY: modified_base
<222> LOCATION: (21)..(21)
<223> OTHER INFORMATION: n=isocytosine

<400> SEQUENCE: 28
gcantctgnc tncanagtng ng                                           22

<210> SEQ ID NO 29
<211> LENGTH: 24
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (3)..(3)
<223> OTHER INFORMATION: n=isocytosine
<220> FEATURE:
<221> NAME/KEY: modified_base
<222> LOCATION: (7)..(7)
<223> OTHER INFORMATION: n=isoguanine
<220> FEATURE:
<221> NAME/KEY: modified_base
<222> LOCATION: (10)..(10)
<223> OTHER INFORMATION: n=isocytosine
<220> FEATURE:
<221> NAME/KEY: modified_base
<222> LOCATION: (13)..(13)
<223> OTHER INFORMATION: n=isoguanine
<220> FEATURE:
<221> NAME/KEY: modified_base
<222> LOCATION: (18)..(18)
<223> OTHER INFORMATION: n=isoguanine
<220> FEATURE:
<221> NAME/KEY: modified_base
<222> LOCATION: (23)..(23)
<223> OTHER INFORMATION: n=isocytosine

<400> SEQUENCE: 29
ctnctgngtn tgntccantg tcnc                                         24

<210> SEQ ID NO 30
<211> LENGTH: 24
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (2)..(2)
<223> OTHER INFORMATION: n=isoguanine
<220> FEATURE:
<221> NAME/KEY: modified_base
<222> LOCATION: (7)..(7)
<223> OTHER INFORMATION: n=isocytosine
<220> FEATURE:
<221> NAME/KEY: modified_base
<222> LOCATION: (12)..(12)
```

```
<223> OTHER INFORMATION: n=isocytosine
<220> FEATURE:
<221> NAME/KEY: modified_base
<222> LOCATION: (15)..(15)
<223> OTHER INFORMATION: n=isoguanine
<220> FEATURE:
<221> NAME/KEY: modified_base
<222> LOCATION: (18)..(18)
<223> OTHER INFORMATION: n=isocytosine
<220> FEATURE:
<221> NAME/KEY: modified_base
<222> LOCATION: (22)..(22)
<223> OTHER INFORMATION: n=isoguanine

<400> SEQUENCE: 30
gngacantgg ancanacnca gnag                                          24

<210> SEQ ID NO 31
<211> LENGTH: 23
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (5)..(5)
<223> OTHER INFORMATION: n=isoguanine
<220> FEATURE:
<221> NAME/KEY: modified_base
<222> LOCATION: (9)..(9)
<223> OTHER INFORMATION: n=isocytosine
<220> FEATURE:
<221> NAME/KEY: modified_base
<222> LOCATION: (11)..(11)
<223> OTHER INFORMATION: n=isoguanine
<220> FEATURE:
<221> NAME/KEY: modified_base
<222> LOCATION: (13)..(13)
<223> OTHER INFORMATION: n=isoguanine
<220> FEATURE:
<221> NAME/KEY: modified_base
<222> LOCATION: (17)..(17)
<223> OTHER INFORMATION: n=isocytosine

<400> SEQUENCE: 31
cgttngaanc nantgcntcg ctc                                           23

<210> SEQ ID NO 32
<211> LENGTH: 23
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (7)..(7)
<223> OTHER INFORMATION: n=isoguanine
<220> FEATURE:
<221> NAME/KEY: modified_base
<222> LOCATION: (11)..(11)
<223> OTHER INFORMATION: n=isocytosine
<220> FEATURE:
<221> NAME/KEY: modified_base
<222> LOCATION: (13)..(13)
<223> OTHER INFORMATION: n=isocytosine
<220> FEATURE:
<221> NAME/KEY: modified_base
<222> LOCATION: (15)..(15)
<223> OTHER INFORMATION: n=isoguanine
<220> FEATURE:
<221> NAME/KEY: modified_base
<222> LOCATION: (19)..(19)
<223> OTHER INFORMATION: n=isocytosine
```

-continued

```
<400> SEQUENCE: 32
gagcgangca ntngnttcna acg                                           23

<210> SEQ ID NO 33
<211> LENGTH: 24
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (3)..(3)
<223> OTHER INFORMATION: n=isoguanine
<220> FEATURE:
<221> NAME/KEY: modified_base
<222> LOCATION: (7)..(7)
<223> OTHER INFORMATION: n=isocytosine
<220> FEATURE:
<221> NAME/KEY: modified_base
<222> LOCATION: (12)..(12)
<223> OTHER INFORMATION: n=isocytosine
<220> FEATURE:
<221> NAME/KEY: modified_base
<222> LOCATION: (14)..(14)
<223> OTHER INFORMATION: n=isoguanine
<220> FEATURE:
<221> NAME/KEY: modified_base
<222> LOCATION: (17)..(17)
<223> OTHER INFORMATION: n=isocytosine
<220> FEATURE:
<221> NAME/KEY: modified_base
<222> LOCATION: (23)..(23)
<223> OTHER INFORMATION: n=isoguanine

<400> SEQUENCE: 33
gtntcgnacc ananctnggt atnc                                          24

<210> SEQ ID NO 34
<211> LENGTH: 24
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (2)..(2)
<223> OTHER INFORMATION: n=isocytosine
<220> FEATURE:
<221> NAME/KEY: modified_base
<222> LOCATION: (8)..(8)
<223> OTHER INFORMATION: n=isoguanine
<220> FEATURE:
<221> NAME/KEY: modified_base
<222> LOCATION: (11)..(11)
<223> OTHER INFORMATION: n=isocytosine
<220> FEATURE:
<221> NAME/KEY: modified_base
<222> LOCATION: (13)..(13)
<223> OTHER INFORMATION: n=isoguanine
<220> FEATURE:
<221> NAME/KEY: modified_base
<222> LOCATION: (18)..(18)
<223> OTHER INFORMATION: n=isoguanine
<220> FEATURE:
<221> NAME/KEY: modified_base
<222> LOCATION: (22)..(22)
<223> OTHER INFORMATION: n=isocytosine

<400> SEQUENCE: 34
gnataccnag ntntggtncg anac                                          24

<210> SEQ ID NO 35
```

```
<211> LENGTH: 24
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (3)..(3)
<223> OTHER INFORMATION: n=isoguanine
<220> FEATURE:
<221> NAME/KEY: modified_base
<222> LOCATION: (6)..(6)
<223> OTHER INFORMATION: n=isocytosine
<220> FEATURE:
<221> NAME/KEY: modified_base
<222> LOCATION: (11)..(11)
<223> OTHER INFORMATION: n=isoguanine
<220> FEATURE:
<221> NAME/KEY: modified_base
<222> LOCATION: (13)..(13)
<223> OTHER INFORMATION: n=isocytosine
<220> FEATURE:
<221> NAME/KEY: modified_base
<222> LOCATION: (17)..(17)
<223> OTHER INFORMATION: n=isocytosine
<220> FEATURE:
<221> NAME/KEY: modified_base
<222> LOCATION: (22)..(22)
<223> OTHER INFORMATION: n=isocytosine

<400> SEQUENCE: 35
gtntgncaca nantcgnttg cntg                                              24

<210> SEQ ID NO 36
<211> LENGTH: 24
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (3)..(3)
<223> OTHER INFORMATION: n=isoguanine
<220> FEATURE:
<221> NAME/KEY: modified_base
<222> LOCATION: (8)..(8)
<223> OTHER INFORMATION: n=isoguanine
<220> FEATURE:
<221> NAME/KEY: modified_base
<222> LOCATION: (12)..(12)
<223> OTHER INFORMATION: n=isoguanine
<220> FEATURE:
<221> NAME/KEY: modified_base
<222> LOCATION: (14)..(14)
<223> OTHER INFORMATION: n=isocytosine
<220> FEATURE:
<221> NAME/KEY: modified_base
<222> LOCATION: (19)..(19)
<223> OTHER INFORMATION: n=isoguanine
<220> FEATURE:
<221> NAME/KEY: modified_base
<222> LOCATION: (22)..(22)
<223> OTHER INFORMATION: n=isocytosine

<400> SEQUENCE: 36
cangcaancg antntgtgnc anac                                              24

<210> SEQ ID NO 37
<211> LENGTH: 24
<212> TYPE: DNA
<213> ORGANISM: Artificial sequence
<220> FEATURE:
<223> OTHER INFORMATION: Description of Artificial Sequence: Synthetic
      orthogonal universal sequence probe
```

```
<220> FEATURE:
<221> NAME/KEY: modified_base
<222> LOCATION: (4)..(4)
<223> OTHER INFORMATION: n=isoguanine
<220> FEATURE:
<221> NAME/KEY: modified_base
<222> LOCATION: (7)..(7)
<223> OTHER INFORMATION: n=isocytosine
<220> FEATURE:
<221> NAME/KEY: modified_base
<222> LOCATION: (11)..(11)
<223> OTHER INFORMATION: n=isoguanine
<220> FEATURE:
<221> NAME/KEY: modified_base
<222> LOCATION: (16)..(16)
<223> OTHER INFORMATION: n=isoguanine
<220> FEATURE:
<221> NAME/KEY: modified_base
<222> LOCATION: (19)..(19)
<223> OTHER INFORMATION: n=isocytosine
<220> FEATURE:
<221> NAME/KEY: modified_base
<222> LOCATION: (23)..(23)
<223> OTHER INFORMATION: n=isoguanine

<400> SEQUENCE: 37
tcanagncac ntgagnganc tcnt                                        24

<210> SEQ ID NO 38
<211> LENGTH: 24
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (2)..(2)
<223> OTHER INFORMATION: n=isocytosine
<220> FEATURE:
<221> NAME/KEY: modified_base
<222> LOCATION: (6)..(6)
<223> OTHER INFORMATION: n=isoguanine
<220> FEATURE:
<221> NAME/KEY: modified_base
<222> LOCATION: (9)..(9)
<223> OTHER INFORMATION: n=isocytosine
<220> FEATURE:
<221> NAME/KEY: modified_base
<222> LOCATION: (14)..(14)
<223> OTHER INFORMATION: n=isocytosine
<220> FEATURE:
<221> NAME/KEY: modified_base
<222> LOCATION: (18)..(18)
<223> OTHER INFORMATION: n=isoguanine
<220> FEATURE:
<221> NAME/KEY: modified_base
<222> LOCATION: (21)..(21)
<223> OTHER INFORMATION: n=isocytosine

<400> SEQUENCE: 38
angagntcnc tcangtgnct ntga                                        24

<210> SEQ ID NO 39
<211> LENGTH: 24
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (2)..(2)
<223> OTHER INFORMATION: n=isoguanine
<220> FEATURE:
<221> NAME/KEY: modified_base
```

```
<222> LOCATION: (7)..(7)
<223> OTHER INFORMATION: n=isocytosine
<220> FEATURE:
<221> NAME/KEY: modified_base
<222> LOCATION: (10)..(10)
<223> OTHER INFORMATION: n=isoguanine
<220> FEATURE:
<221> NAME/KEY: modified_base
<222> LOCATION: (13)..(13)
<223> OTHER INFORMATION: n=isocytosine
<220> FEATURE:
<221> NAME/KEY: modified_base
<222> LOCATION: (18)..(18)
<223> OTHER INFORMATION: n=isocytosine
<220> FEATURE:
<221> NAME/KEY: modified_base
<222> LOCATION: (22)..(22)
<223> OTHER INFORMATION: n=isoguanine

<400> SEQUENCE: 39
gngtcancgn atntcagntc anct                                      24

<210> SEQ ID NO 40
<211> LENGTH: 24
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (3)..(3)
<223> OTHER INFORMATION: n=isocytosine
<220> FEATURE:
<221> NAME/KEY: modified_base
<222> LOCATION: (7)..(7)
<223> OTHER INFORMATION: n=isoguanine
<220> FEATURE:
<221> NAME/KEY: modified_base
<222> LOCATION: (12)..(12)
<223> OTHER INFORMATION: n=isoguanine
<220> FEATURE:
<221> NAME/KEY: modified_base
<222> LOCATION: (15)..(15)
<223> OTHER INFORMATION: n=isocytosine
<220> FEATURE:
<221> NAME/KEY: modified_base
<222> LOCATION: (18)..(18)
<223> OTHER INFORMATION: n=isoguanine
<220> FEATURE:
<221> NAME/KEY: modified_base
<222> LOCATION: (23)..(23)
<223> OTHER INFORMATION: n=isocytosine

<400> SEQUENCE: 40
agntganctg anatncgntg acnc                                      24

<210> SEQ ID NO 41
<211> LENGTH: 25
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (3)..(3)
<223> OTHER INFORMATION: n=isoguanine
<220> FEATURE:
<221> NAME/KEY: modified_base
<222> LOCATION: (6)..(6)
<223> OTHER INFORMATION: n=isoguanine
<220> FEATURE:
<221> NAME/KEY: modified_base
<222> LOCATION: (11)..(11)
<223> OTHER INFORMATION: n=isocytosine
```

```
<220> FEATURE:
<221> NAME/KEY: modified_base
<222> LOCATION: (16)..(16)
<223> OTHER INFORMATION: n=isocytosine
<220> FEATURE:
<221> NAME/KEY: modified_base
<222> LOCATION: (21)..(21)
<223> OTHER INFORMATION: n=isocytosine
<220> FEATURE:
<221> NAME/KEY: modified_base
<222> LOCATION: (24)..(24)
<223> OTHER INFORMATION: n=isocytosine

<400> SEQUENCE: 41
canganctac ngacanagag ntgnc                                              25

<210> SEQ ID NO 42
<211> LENGTH: 25
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (2)..(2)
<223> OTHER INFORMATION: n=isoguanine
<220> FEATURE:
<221> NAME/KEY: modified_base
<222> LOCATION: (5)..(5)
<223> OTHER INFORMATION: n=isoguanine
<220> FEATURE:
<221> NAME/KEY: modified_base
<222> LOCATION: (10)..(10)
<223> OTHER INFORMATION: n=isoguanine
<220> FEATURE:
<221> NAME/KEY: modified_base
<222> LOCATION: (15)..(15)
<223> OTHER INFORMATION: n=isoguanine
<220> FEATURE:
<221> NAME/KEY: modified_base
<222> LOCATION: (20)..(20)
<223> OTHER INFORMATION: n=isocytosine
<220> FEATURE:
<221> NAME/KEY: modified_base
<222> LOCATION: (23)..(23)
<223> OTHER INFORMATION: n=isocytosine

<400> SEQUENCE: 42
gncanctctn tgtcngtagn tcntg                                              25

<210> SEQ ID NO 43
<211> LENGTH: 23
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (2)..(2)
<223> OTHER INFORMATION: n=isocytosine
<220> FEATURE:
<221> NAME/KEY: modified_base
<222> LOCATION: (6)..(6)
<223> OTHER INFORMATION: n=isocytosine
<220> FEATURE:
<221> NAME/KEY: modified_base
<222> LOCATION: (11)..(11)
<223> OTHER INFORMATION: n=isoguanine
<220> FEATURE:
<221> NAME/KEY: modified_base
<222> LOCATION: (13)..(13)
<223> OTHER INFORMATION: n=isocytosine
<220> FEATURE:
<221> NAME/KEY: modified_base
```

-continued

```
<222> LOCATION: (17)..(17)
<223> OTHER INFORMATION: n=isoguanine
<220> FEATURE:
<221> NAME/KEY: modified_base
<222> LOCATION: (21)..(21)
<223> OTHER INFORMATION: n=isocytosine

<400> SEQUENCE: 43
gngttnactc ncnaagnttc naa                                          23

<210> SEQ ID NO 44
<211> LENGTH: 23
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (3)..(3)
<223> OTHER INFORMATION: n=isoguanine
<220> FEATURE:
<221> NAME/KEY: modified_base
<222> LOCATION: (7)..(7)
<223> OTHER INFORMATION: n=isocytosine
<220> FEATURE:
<221> NAME/KEY: modified_base
<222> LOCATION: (11)..(11)
<223> OTHER INFORMATION: n=isoguanine
<220> FEATURE:
<221> NAME/KEY: modified_base
<222> LOCATION: (13)..(13)
<223> OTHER INFORMATION: n=isocytosine
<220> FEATURE:
<221> NAME/KEY: modified_base
<222> LOCATION: (18)..(18)
<223> OTHER INFORMATION: n=isoguanine
<220> FEATURE:
<221> NAME/KEY: modified_base
<222> LOCATION: (22)..(22)
<223> OTHER INFORMATION: n=isoguanine

<400> SEQUENCE: 44
ttngaanctt ngngagtnaa cnc                                          23

<210> SEQ ID NO 45
<211> LENGTH: 23
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (2)..(2)
<223> OTHER INFORMATION: n=isocytosine
<220> FEATURE:
<221> NAME/KEY: modified_base
<222> LOCATION: (6)..(6)
<223> OTHER INFORMATION: n=isocytosine
<220> FEATURE:
<221> NAME/KEY: modified_base
<222> LOCATION: (11)..(11)
<223> OTHER INFORMATION: n=isoguanine
<220> FEATURE:
<221> NAME/KEY: modified_base
<222> LOCATION: (16)..(16)
<223> OTHER INFORMATION: n=isoguanine
<220> FEATURE:
<221> NAME/KEY: modified_base
<222> LOCATION: (20)..(20)
<223> OTHER INFORMATION: n=isocytosine
<220> FEATURE:
<221> NAME/KEY: modified_base
<222> LOCATION: (22)..(22)
<223> OTHER INFORMATION: n=isocytosine
```

```
<400> SEQUENCE: 45
tncgtnagga natccnacan gna                                              23

<210> SEQ ID NO 46
<211> LENGTH: 23
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (2)..(2)
<223> OTHER INFORMATION: n=isoguanine
<220> FEATURE:
<221> NAME/KEY: modified_base
<222> LOCATION: (4)..(4)
<223> OTHER INFORMATION: n=isoguanine
<220> FEATURE:
<221> NAME/KEY: modified_base
<222> LOCATION: (8)..(8)
<223> OTHER INFORMATION: n=isocytosine
<220> FEATURE:
<221> NAME/KEY: modified_base
<222> LOCATION: (13)..(13)
<223> OTHER INFORMATION: n=isocytosine
<220> FEATURE:
<221> NAME/KEY: modified_base
<222> LOCATION: (18)..(18)
<223> OTHER INFORMATION: n=isoguanine
<220> FEATURE:
<221> NAME/KEY: modified_base
<222> LOCATION: (22)..(22)
<223> OTHER INFORMATION: n=isoguanine

<400> SEQUENCE: 46
tncntgtngg atntcctnac gna                                              23

<210> SEQ ID NO 47
<211> LENGTH: 23
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (3)..(3)
<223> OTHER INFORMATION: n=isoguanine
<220> FEATURE:
<221> NAME/KEY: modified_base
<222> LOCATION: (7)..(7)
<223> OTHER INFORMATION: n=isocytosine
<220> FEATURE:
<221> NAME/KEY: modified_base
<222> LOCATION: (10)..(10)
<223> OTHER INFORMATION: n=isocytosine
<220> FEATURE:
<221> NAME/KEY: modified_base
<222> LOCATION: (13)..(13)
<223> OTHER INFORMATION: n=isocytosine
<220> FEATURE:
<221> NAME/KEY: modified_base
<222> LOCATION: (18)..(18)
<223> OTHER INFORMATION: n=isoguanine
<220> FEATURE:
<221> NAME/KEY: modified_base
<222> LOCATION: (22)..(22)
<223> OTHER INFORMATION: n=isoguanine

<400> SEQUENCE: 47
ccnaagngtn tgnctgtnag tnc                                              23
```

```
<210> SEQ ID NO 48
<211> LENGTH: 23
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (2)..(2)
<223> OTHER INFORMATION: n=isocytosine
<220> FEATURE:
<221> NAME/KEY: modified_base
<222> LOCATION: (6)..(6)
<223> OTHER INFORMATION: n=isocytosine
<220> FEATURE:
<221> NAME/KEY: modified_base
<222> LOCATION: (11)..(11)
<223> OTHER INFORMATION: n=isoguanine
<220> FEATURE:
<221> NAME/KEY: modified_base
<222> LOCATION: (14)..(14)
<223> OTHER INFORMATION: n=isoguanine
<220> FEATURE:
<221> NAME/KEY: modified_base
<222> LOCATION: (17)..(17)
<223> OTHER INFORMATION: n=isoguanine
<220> FEATURE:
<221> NAME/KEY: modified_base
<222> LOCATION: (21)..(21)
<223> OTHER INFORMATION: n=isocytosine

<400> SEQUENCE: 48
gnactnacag ncanacnctt ngg                                           23

<210> SEQ ID NO 49
<211> LENGTH: 23
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (2)..(2)
<223> OTHER INFORMATION: n=isocytosine
<220> FEATURE:
<221> NAME/KEY: modified_base
<222> LOCATION: (7)..(7)
<223> OTHER INFORMATION: n=isoguanine
<220> FEATURE:
<221> NAME/KEY: modified_base
<222> LOCATION: (12)..(12)
<223> OTHER INFORMATION: n=isocytosine
<220> FEATURE:
<221> NAME/KEY: modified_base
<222> LOCATION: (17)..(17)
<223> OTHER INFORMATION: n=isocytosine
<220> FEATURE:
<221> NAME/KEY: modified_base
<222> LOCATION: (20)..(20)
<223> OTHER INFORMATION: n=isoguanine
<220> FEATURE:
<221> NAME/KEY: modified_base
<222> LOCATION: (23)..(23)
<223> OTHER INFORMATION: n=isoguanine

<400> SEQUENCE: 49
gngttcnaag cntgacngan ttn                                           23

<210> SEQ ID NO 50
<211> LENGTH: 23
<212> TYPE: DNA
<213> ORGANISM: Artificial sequence
<220> FEATURE:
<223> OTHER INFORMATION: Description of Artificial Sequence: Synthetic
``` orthogonal universal sequence probe
<220> FEATURE:
<221> NAME/KEY: modified_base
<222> LOCATION: (1)..(1)
<223> OTHER INFORMATION: n=isocytosine
<220> FEATURE:
<221> NAME/KEY: modified_base
<222> LOCATION: (4)..(4)
<223> OTHER INFORMATION: n=isocytosine
<220> FEATURE:
<221> NAME/KEY: modified_base
<222> LOCATION: (7)..(7)
<223> OTHER INFORMATION: n=isoguanine
<220> FEATURE:
<221> NAME/KEY: modified_base
<222> LOCATION: (12)..(12)
<223> OTHER INFORMATION: n=isoguanine
<220> FEATURE:
<221> NAME/KEY: modified_base
<222> LOCATION: (17)..(17)
<223> OTHER INFORMATION: n=isocytosine
<220> FEATURE:
<221> NAME/KEY: modified_base
<222> LOCATION: (22)..(22)
<223> OTHER INFORMATION: n=isoguanine

<400> SEQUENCE: 50
naantcngtc angcttngaa cnc                                              23

<210> SEQ ID NO 51
<211> LENGTH: 24
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (3)..(3)
<223> OTHER INFORMATION: n=isocytosine
<220> FEATURE:
<221> NAME/KEY: modified_base
<222> LOCATION: (5)..(5)
<223> OTHER INFORMATION: n=isoguanine
<220> FEATURE:
<221> NAME/KEY: modified_base
<222> LOCATION: (10)..(10)
<223> OTHER INFORMATION: n=isocytosine
<220> FEATURE:
<221> NAME/KEY: modified_base
<222> LOCATION: (15)..(15)
<223> OTHER INFORMATION: n=isoguanine
<220> FEATURE:
<221> NAME/KEY: modified_base
<222> LOCATION: (20)..(20)
<223> OTHER INFORMATION: n=isoguanine
<220> FEATURE:
<221> NAME/KEY: modified_base
<222> LOCATION: (23)..(23)
<223> OTHER INFORMATION: n=isoguanine

<400> SEQUENCE: 51
acntncttgn gtcanacctn ganc                                             24

<210> SEQ ID NO 52
<211> LENGTH: 24
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (2)..(2)
<223> OTHER INFORMATION: n=isocytosine
<220> FEATURE:

```
<221> NAME/KEY: modified_base
<222> LOCATION: (5)..(5)
<223> OTHER INFORMATION: n=isocytosine
<220> FEATURE:
<221> NAME/KEY: modified_base
<222> LOCATION: (10)..(10)
<223> OTHER INFORMATION: n=isocytosine
<220> FEATURE:
<221> NAME/KEY: modified_base
<222> LOCATION: (15)..(15)
<223> OTHER INFORMATION: n=isoguanine
<220> FEATURE:
<221> NAME/KEY: modified_base
<222> LOCATION: (20)..(20)
<223> OTHER INFORMATION: n=isocytosine
<220> FEATURE:
<221> NAME/KEY: modified_base
<222> LOCATION: (22)..(22)
<223> OTHER INFORMATION: n=isoguanine

<400> SEQUENCE: 52
gntcnaggtn tgacncaagn angt                                          24

<210> SEQ ID NO 53
<211> LENGTH: 23
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (2)..(2)
<223> OTHER INFORMATION: n=isocytosine
<220> FEATURE:
<221> NAME/KEY: modified_base
<222> LOCATION: (7)..(7)
<223> OTHER INFORMATION: n=isoguanine
<220> FEATURE:
<221> NAME/KEY: modified_base
<222> LOCATION: (11)..(11)
<223> OTHER INFORMATION: n=isoguanine
<220> FEATURE:
<221> NAME/KEY: modified_base
<222> LOCATION: (15)..(15)
<223> OTHER INFORMATION: n=isocytosine
<220> FEATURE:
<221> NAME/KEY: modified_base
<222> LOCATION: (18)..(18)
<223> OTHER INFORMATION: n=isocytosine
<220> FEATURE:
<221> NAME/KEY: modified_base
<222> LOCATION: (23)..(23)
<223> OTHER INFORMATION: n=isoguanine

<400> SEQUENCE: 53
gnaggtncca ntcgntanga tgn                                           23

<210> SEQ ID NO 54
<211> LENGTH: 23
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (1)..(1)
<223> OTHER INFORMATION: n=isocytosine
<220> FEATURE:
<221> NAME/KEY: modified_base
<222> LOCATION: (6)..(6)
<223> OTHER INFORMATION: n=isoguanine
<220> FEATURE:
<221> NAME/KEY: modified_base
<222> LOCATION: (9)..(9)
```

```
<223> OTHER INFORMATION: n=isoguanine
<220> FEATURE:
<221> NAME/KEY: modified_base
<222> LOCATION: (13)..(13)
<223> OTHER INFORMATION: n=isocytosine
<220> FEATURE:
<221> NAME/KEY: modified_base
<222> LOCATION: (17)..(17)
<223> OTHER INFORMATION: n=isocytosine
<220> FEATURE:
<221> NAME/KEY: modified_base
<222> LOCATION: (22)..(22)
<223> OTHER INFORMATION: n=isoguanine

<400> SEQUENCE: 54
ncatcntanc gantggnacc tnc                                                 23

<210> SEQ ID NO 55
<211> LENGTH: 24
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (5)..(5)
<223> OTHER INFORMATION: n=isocytosine
<220> FEATURE:
<221> NAME/KEY: modified_base
<222> LOCATION: (10)..(10)
<223> OTHER INFORMATION: n=isocytosine
<220> FEATURE:
<221> NAME/KEY: modified_base
<222> LOCATION: (13)..(13)
<223> OTHER INFORMATION: n=isoguanine
<220> FEATURE:
<221> NAME/KEY: modified_base
<222> LOCATION: (16)..(16)
<223> OTHER INFORMATION: n=isoguanine
<220> FEATURE:
<221> NAME/KEY: modified_base
<222> LOCATION: (20)..(20)
<223> OTHER INFORMATION: n=isocytosine

<400> SEQUENCE: 55
tctgngtgan acntgntctn ggct                                                24

<210> SEQ ID NO 56
<211> LENGTH: 24
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (5)..(5)
<223> OTHER INFORMATION: n=isoguanine
<220> FEATURE:
<221> NAME/KEY: modified_base
<222> LOCATION: (9)..(9)
<223> OTHER INFORMATION: n=isocytosine
<220> FEATURE:
<221> NAME/KEY: modified_base
<222> LOCATION: (12)..(12)
<223> OTHER INFORMATION: n=isocytosine
<220> FEATURE:
<221> NAME/KEY: modified_base
<222> LOCATION: (15)..(15)
<223> OTHER INFORMATION: n=isoguanine
<220> FEATURE:
<221> NAME/KEY: modified_base
<222> LOCATION: (20)..(20)
<223> OTHER INFORMATION: n=isoguanine
```

-continued

```
<400> SEQUENCE: 56
agccnaganc angtntcacn caga                                              24

<210> SEQ ID NO 57
<211> LENGTH: 23
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (2)..(2)
<223> OTHER INFORMATION: n=isocytosine
<220> FEATURE:
<221> NAME/KEY: modified_base
<222> LOCATION: (7)..(7)
<223> OTHER INFORMATION: n=isocytosine
<220> FEATURE:
<221> NAME/KEY: modified_base
<222> LOCATION: (10)..(10)
<223> OTHER INFORMATION: n=isocytosine
<220> FEATURE:
<221> NAME/KEY: modified_base
<222> LOCATION: (12)..(12)
<223> OTHER INFORMATION: n=isoguanine
<220> FEATURE:
<221> NAME/KEY: modified_base
<222> LOCATION: (16)..(16)
<223> OTHER INFORMATION: n=isoguanine
<220> FEATURE:
<221> NAME/KEY: modified_base
<222> LOCATION: (21)..(21)
<223> OTHER INFORMATION: n=isocytosine

<400> SEQUENCE: 57
angtgtnttn cnctcnatgg naa                                               23

<210> SEQ ID NO 58
<211> LENGTH: 23
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (3)..(3)
<223> OTHER INFORMATION: n=isoguanine
<220> FEATURE:
<221> NAME/KEY: modified_base
<222> LOCATION: (8)..(8)
<223> OTHER INFORMATION: n=isocytosine
<220> FEATURE:
<221> NAME/KEY: modified_base
<222> LOCATION: (12)..(12)
<223> OTHER INFORMATION: n=isocytosine
<220> FEATURE:
<221> NAME/KEY: modified_base
<222> LOCATION: (14)..(14)
<223> OTHER INFORMATION: n=isoguanine
<220> FEATURE:
<221> NAME/KEY: modified_base
<222> LOCATION: (17)..(17)
<223> OTHER INFORMATION: n=isoguanine
<220> FEATURE:
<221> NAME/KEY: modified_base
<222> LOCATION: (22)..(22)
<223> OTHER INFORMATION: n=isoguanine

<400> SEQUENCE: 58
ttnccatnga gngnaanaca cnt                                               23

<210> SEQ ID NO 59
```

```
<211> LENGTH: 23
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (2)..(2)
<223> OTHER INFORMATION: n=isoguanine
<220> FEATURE:
<221> NAME/KEY: modified_base
<222> LOCATION: (5)..(5)
<223> OTHER INFORMATION: n=isoguanine
<220> FEATURE:
<221> NAME/KEY: modified_base
<222> LOCATION: (8)..(8)
<223> OTHER INFORMATION: n=isoguanine
<220> FEATURE:
<221> NAME/KEY: modified_base
<222> LOCATION: (13)..(13)
<223> OTHER INFORMATION: n=isoguanine
<220> FEATURE:
<221> NAME/KEY: modified_base
<222> LOCATION: (17)..(17)
<223> OTHER INFORMATION: n=isocytosine
<220> FEATURE:
<221> NAME/KEY: modified_base
<222> LOCATION: (22)..(22)
<223> OTHER INFORMATION: n=isocytosine

<400> SEQUENCE: 59
cnctntcnca gtntagnctg cnt                                             23

<210> SEQ ID NO 60
<211> LENGTH: 23
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (2)..(2)
<223> OTHER INFORMATION: n=isoguanine
<220> FEATURE:
<221> NAME/KEY: modified_base
<222> LOCATION: (7)..(7)
<223> OTHER INFORMATION: n=isoguanine
<220> FEATURE:
<221> NAME/KEY: modified_base
<222> LOCATION: (11)..(11)
<223> OTHER INFORMATION: n=isocytosine
<220> FEATURE:
<221> NAME/KEY: modified_base
<222> LOCATION: (16)..(16)
<223> OTHER INFORMATION: n=isocytosine
<220> FEATURE:
<221> NAME/KEY: modified_base
<222> LOCATION: (19)..(19)
<223> OTHER INFORMATION: n=isocytosine
<220> FEATURE:
<221> NAME/KEY: modified_base
<222> LOCATION: (22)..(22)
<223> OTHER INFORMATION: n=isocytosine

<400> SEQUENCE: 60
angcagncta nactgngana gng                                             23

<210> SEQ ID NO 61
<211> LENGTH: 24
<212> TYPE: DNA
<213> ORGANISM: Artificial sequence
<220> FEATURE:
<223> OTHER INFORMATION: Description of Artificial Sequence: Synthetic
      orthogonal universal sequence probe
```

```
<220> FEATURE:
<221> NAME/KEY: modified_base
<222> LOCATION: (2)..(2)
<223> OTHER INFORMATION: n=isocytosine
<220> FEATURE:
<221> NAME/KEY: modified_base
<222> LOCATION: (7)..(7)
<223> OTHER INFORMATION: n=isguanine
<220> FEATURE:
<221> NAME/KEY: modified_base
<222> LOCATION: (12)..(12)
<223> OTHER INFORMATION: n=isoguanine
<220> FEATURE:
<221> NAME/KEY: modified_base
<222> LOCATION: (17)..(17)
<223> OTHER INFORMATION: n=isocytosine
<220> FEATURE:
<221> NAME/KEY: modified_base
<222> LOCATION: (19)..(19)
<223> OTHER INFORMATION: n=isocytosine

<400> SEQUENCE: 61
gntgtcncta cntgtgngnt ttgc                                              24

<210> SEQ ID NO 62
<211> LENGTH: 24
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (6)..(6)
<223> OTHER INFORMATION: n=isoguanine
<220> FEATURE:
<221> NAME/KEY: modified_base
<222> LOCATION: (8)..(8)
<223> OTHER INFORMATION: n=isoguanine
<220> FEATURE:
<221> NAME/KEY: modified_base
<222> LOCATION: (13)..(13)
<223> OTHER INFORMATION: n=isocytosine
<220> FEATURE:
<221> NAME/KEY: modified_base
<222> LOCATION: (18)..(18)
<223> OTHER INFORMATION: n=isocytosine
<220> FEATURE:
<221> NAME/KEY: modified_base
<222> LOCATION: (23)..(23)
<223> OTHER INFORMATION: n=isoguanine

<400> SEQUENCE: 62
gcaaancnca cangtagnga canc                                              24

<210> SEQ ID NO 63
<211> LENGTH: 24
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (5)..(5)
<223> OTHER INFORMATION: n=isocytosine
<220> FEATURE:
<221> NAME/KEY: modified_base
<222> LOCATION: (9)..(9)
<223> OTHER INFORMATION: n=isocytosine
<220> FEATURE:
<221> NAME/KEY: modified_base
<222> LOCATION: (11)..(11)
<223> OTHER INFORMATION: n=isoguanine
<220> FEATURE:
<221> NAME/KEY: modified_base
```

```
<222> LOCATION: (16)..(16)
<223> OTHER INFORMATION: n=isocytosine
<220> FEATURE:
<221> NAME/KEY: modified_base
<222> LOCATION: (18)..(18)
<223> OTHER INFORMATION: n=isocytosine
<220> FEATURE:
<221> NAME/KEY: modified_base
<222> LOCATION: (22)..(22)
<223> OTHER INFORMATION: n=isoguanine

<400> SEQUENCE: 63
cgaangctnt naggtnanag cntc                                              24

<210> SEQ ID NO 64
<211> LENGTH: 24
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (3)..(3)
<223> OTHER INFORMATION: n=isocytosine
<220> FEATURE:
<221> NAME/KEY: modified_base
<222> LOCATION: (7)..(7)
<223> OTHER INFORMATION: n=isoguanine
<220> FEATURE:
<221> NAME/KEY: modified_base
<222> LOCATION: (9)..(9)
<223> OTHER INFORMATION: n=isoguanine
<220> FEATURE:
<221> NAME/KEY: modified_base
<222> LOCATION: (14)..(14)
<223> OTHER INFORMATION: n=isocytosine
<220> FEATURE:
<221> NAME/KEY: modified_base
<222> LOCATION: (16)..(16)
<223> OTHER INFORMATION: n=isoguanine
<220> FEATURE:
<221> NAME/KEY: modified_base
<222> LOCATION: (20)..(20)
<223> OTHER INFORMATION: n=isoguanine

<400> SEQUENCE: 64
gangctntna cctnanagcn ttcg                                              24

<210> SEQ ID NO 65
<211> LENGTH: 22
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (3)..(3)
<223> OTHER INFORMATION: n=isoguanine
<220> FEATURE:
<221> NAME/KEY: modified_base
<222> LOCATION: (7)..(7)
<223> OTHER INFORMATION: n=isocytosine
<220> FEATURE:
<221> NAME/KEY: modified_base
<222> LOCATION: (11)..(11)
<223> OTHER INFORMATION: n=isoguanine
<220> FEATURE:
<221> NAME/KEY: modified_base
<222> LOCATION: (15)..(15)
<223> OTHER INFORMATION: n=isoguanine
<220> FEATURE:
<221> NAME/KEY: modified_base
<222> LOCATION: (19)..(19)
<223> OTHER INFORMATION: n=isocytosine
```

```
<220> FEATURE:
<221> NAME/KEY: modified_base
<222> LOCATION: (22)..(22)
<223> OTHER INFORMATION: n=isocytosine

<400> SEQUENCE: 65
gtnctcnaga ngctnatgnc gn                                              22

<210> SEQ ID NO 66
<211> LENGTH: 22
<212> TYPE: DNA
<213> ORGANISM: Artificial sequence
<220> FEATURE:
<223> OTHER INFORMATION: Description of Artificial Sequence: Synthetic
      orthogonal universal sequence probe
<220> FEATURE:
<221> NAME/KEY: modified_base
<222> LOCATION: (1)..(1)
<223> OTHER INFORMATION: n=isoguanine
<220> FEATURE:
<221> NAME/KEY: modified_base
<222> LOCATION: (4)..(4)
<223> OTHER INFORMATION: n=isoguanine
<220> FEATURE:
<221> NAME/KEY: modified_base
<222> LOCATION: (8)..(8)
<223> OTHER INFORMATION: n=isocytosine
<220> FEATURE:
<221> NAME/KEY: modified_base
<222> LOCATION: (12)..(12)
<223> OTHER INFORMATION: n=isocytosine
<220> FEATURE:
<221> NAME/KEY: modified_base
<222> LOCATION: (16)..(16)
<223> OTHER INFORMATION: n=isoguanine
<220> FEATURE:
<221> NAME/KEY: modified_base
<222> LOCATION: (20)..(20)
<223> OTHER INFORMATION: n=isocytosine

<400> SEQUENCE: 66
ncgncatnag cntctngagn ac                                              22

<210> SEQ ID NO 67
<211> LENGTH: 25
<212> TYPE: DNA
<213> ORGANISM: Artificial sequence
<220> FEATURE:
<223> OTHER INFORMATION: Description of Artificial Sequence: Synthetic
      "ZipCode" probe sequence

<400> SEQUENCE: 67
gacattcgcg atcgccgccc gcttt                                           25

<210> SEQ ID NO 68
<211> LENGTH: 25
<212> TYPE: DNA
<213> ORGANISM: Artificial sequence
<220> FEATURE:
<223> OTHER INFORMATION: Description of Artificial Sequence: Synthetic
      "ZipCode" probe sequence

<400> SEQUENCE: 68
aaagcgggcg gcgatcgcga atgtc                                           25

<210> SEQ ID NO 69
<211> LENGTH: 25
<212> TYPE: DNA
<213> ORGANISM: Artificial sequence
<220> FEATURE:
<223> OTHER INFORMATION: Description of Artificial Sequence: Synthetic
      "ZipCode" probe sequence
```

-continued

<400> SEQUENCE: 69
caccgccagc tcggcttcga gttcg                                              25

<210> SEQ ID NO 70
<211> LENGTH: 25
<212> TYPE: DNA
<213> ORGANISM: Artificial sequence
<220> FEATURE:
<223> OTHER INFORMATION: Description of Artificial Sequence: Synthetic
      "ZipCode" probe sequence

<400> SEQUENCE: 70
cgaactcgaa gccgagctgg cggtg                                              25

<210> SEQ ID NO 71
<211> LENGTH: 25
<212> TYPE: DNA
<213> ORGANISM: Artificial sequence
<220> FEATURE:
<223> OTHER INFORMATION: Description of Artificial Sequence: Synthetic
      "ZipCode" probe sequence

<400> SEQUENCE: 71
gaacctttcg cttcaccggc cgatc                                              25

<210> SEQ ID NO 72
<211> LENGTH: 25
<212> TYPE: DNA
<213> ORGANISM: Artificial sequence
<220> FEATURE:
<223> OTHER INFORMATION: Description of Artificial Sequence: Synthetic
      "ZipCode" probe sequence

<400> SEQUENCE: 72
gatcggccgg tgaagcgaaa ggttc                                              25

<210> SEQ ID NO 73
<211> LENGTH: 25
<212> TYPE: DNA
<213> ORGANISM: Artificial sequence
<220> FEATURE:
<223> OTHER INFORMATION: Description of Artificial Sequence: Synthetic
      "ZipCode" probe sequence

<400> SEQUENCE: 73
ccggctttga actgctcacc gatct                                              25

<210> SEQ ID NO 74
<211> LENGTH: 25
<212> TYPE: DNA
<213> ORGANISM: Artificial sequence
<220> FEATURE:
<223> OTHER INFORMATION: Description of Artificial Sequence: Synthetic
      "ZipCode" probe sequence

<400> SEQUENCE: 74
agatcggtga gcagttcaaa gccgg                                              25

<210> SEQ ID NO 75
<211> LENGTH: 25
<212> TYPE: DNA
<213> ORGANISM: Artificial sequence
<220> FEATURE:
<223> OTHER INFORMATION: Description of Artificial Sequence: Synthetic
      "ZipCode" probe sequence

<400> SEQUENCE: 75

-continued agcagcagtg acaatgccac cgccg                    25

<210> SEQ ID NO 76
<211> LENGTH: 25
<212> TYPE: DNA
<213> ORGANISM: Artificial sequence
<220> FEATURE:
<223> OTHER INFORMATION: Description of Artificial Sequence: Synthetic
      "ZipCode" probe sequence

<400> SEQUENCE: 76
cggcggtggc attgtcactg ctgct                    25

<210> SEQ ID NO 77
<211> LENGTH: 25
<212> TYPE: DNA
<213> ORGANISM: Artificial sequence
<220> FEATURE:
<223> OTHER INFORMATION: Description of Artificial Sequence: Synthetic
      "ZipCode" probe sequence

<400> SEQUENCE: 77
tcgcccgcgg acaccgagaa ttcga                    25

<210> SEQ ID NO 78
<211> LENGTH: 25
<212> TYPE: DNA
<213> ORGANISM: Artificial sequence
<220> FEATURE:
<223> OTHER INFORMATION: Description of Artificial Sequence: Synthetic
      "ZipCode" probe sequence

<400> SEQUENCE: 78
tcgaattctc ggtgtccgcg ggcga                    25

<210> SEQ ID NO 79
<211> LENGTH: 25
<212> TYPE: DNA
<213> ORGANISM: Artificial sequence
<220> FEATURE:
<223> OTHER INFORMATION: Description of Artificial Sequence: Synthetic
      "ZipCode" probe sequence

<400> SEQUENCE: 79
caccaccagt gccgctacca caacg                    25

<210> SEQ ID NO 80
<211> LENGTH: 25
<212> TYPE: DNA
<213> ORGANISM: Artificial sequence
<220> FEATURE:
<223> OTHER INFORMATION: Description of Artificial Sequence: Synthetic
      "ZipCode" probe sequence

<400> SEQUENCE: 80
cgttgtggta gcggcactgg tggtg                    25

<210> SEQ ID NO 81
<211> LENGTH: 25
<212> TYPE: DNA
<213> ORGANISM: Artificial sequence
<220> FEATURE:
<223> OTHER INFORMATION: Description of Artificial Sequence: Synthetic
      "ZipCode" probe sequence

<400> SEQUENCE: 81
cggcggtctt cacgctcaac agcag                    25

```
<210> SEQ ID NO 82
<211> LENGTH: 25
<212> TYPE: DNA
<213> ORGANISM: Artificial sequence
<220> FEATURE:
<223> OTHER INFORMATION: Description of Artificial Sequence: Synthetic
      "ZipCode" probe sequence

<400> SEQUENCE: 82
ctgctgttga gcgtgaagac cgccg                                              25

<210> SEQ ID NO 83
<211> LENGTH: 25
<212> TYPE: DNA
<213> ORGANISM: Artificial sequence
<220> FEATURE:
<223> OTHER INFORMATION: Description of Artificial Sequence: Synthetic
      "ZipCode" probe sequence

<400> SEQUENCE: 83
agccgcgaac accacgatcg accgg                                              25

<210> SEQ ID NO 84
<211> LENGTH: 25
<212> TYPE: DNA
<213> ORGANISM: Artificial sequence
<220> FEATURE:
<223> OTHER INFORMATION: Description of Artificial Sequence: Synthetic
      "ZipCode" probe sequence

<400> SEQUENCE: 84
ccggtcgatc gtggtgttcg cggct                                              25

<210> SEQ ID NO 85
<211> LENGTH: 25
<212> TYPE: DNA
<213> ORGANISM: Artificial sequence
<220> FEATURE:
<223> OTHER INFORMATION: Description of Artificial Sequence: Synthetic
      "ZipCode" probe sequence

<400> SEQUENCE: 85
taccggcggc agcaccagcg gtaac                                              25

<210> SEQ ID NO 86
<211> LENGTH: 25
<212> TYPE: DNA
<213> ORGANISM: Artificial sequence
<220> FEATURE:
<223> OTHER INFORMATION: Description of Artificial Sequence: Synthetic
      "ZipCode" probe sequence

<400> SEQUENCE: 86
gttaccgctg gtgctgccgc cggta                                              25
```